US007884093B2

(12) United States Patent
Creasy et al.

(10) Patent No.: US 7,884,093 B2
(45) Date of Patent: *Feb. 8, 2011

(54) PROGESTERONE FOR THE TREATMENT OR PREVENTION OF SPONTANEOUS PRETERM BIRTH

(76) Inventors: George Creasy, 539 Brian Dean Dr., Glen Gardner, NJ (US) 08826; John M. O'Brien, Jr., 2109 Woodley Cir., Lexington, KY (US) 40502; Emily A. DeFranco, 458 Hidden Valley La., Cincinnati, OH (US) 45215; Kenneth N. Muse, 2104 Woodbridge Way, Lexington, KY (US) 40515-1115

( * ) Notice: Subject to any disclaimer, the term of this patent is extended or adjusted under 35 U.S.C. 154(b) by 0 days.

This patent is subject to a terminal disclaimer.

(21) Appl. No.: 12/497,879

(22) Filed: Jul. 6, 2009

(65) Prior Publication Data

US 2009/0264395 A1  Oct. 22, 2009

Related U.S. Application Data

(63) Continuation of application No. 12/024,756, filed on Feb. 1, 2008.

(60) Provisional application No. 60/888,480, filed on Feb. 6, 2007, provisional application No. 60/973,667, filed on Sep. 19, 2007.

(51) Int. Cl.
*A61K 31/56* (2006.01)
*C07D 215/04* (2006.01)
*A61M 31/00* (2006.01)

(52) U.S. Cl. ............................ 514/177; 540/2; 604/500; 604/522

(58) Field of Classification Search ................. 514/177; 540/2; 604/500, 522
See application file for complete search history.

(56) References Cited

U.S. PATENT DOCUMENTS

| | | | |
|---|---|---|---|
| 5,543,150 A | 8/1996 | Bologna et al. | |
| 5,744,463 A | 4/1998 | Blair | |
| 5,830,848 A | 11/1998 | Harrison et al. | 514/2 |
| 5,895,783 A | 4/1999 | Garfield et al. | 514/12 |
| 5,910,482 A | 6/1999 | Yallampalli et al. | 514/12 |
| 5,948,762 A | 9/1999 | Garfield et al. | 514/12 |
| 5,962,413 A | 10/1999 | Garfield et al. | 514/12 |
| 5,965,529 A | 10/1999 | Garfield et al. | 514/12 |
| 6,040,340 A | 3/2000 | Chwalisz et al. | |
| 6,333,350 B1 | 12/2001 | Chwalisz et al. | 514/509 |
| 6,375,970 B1 | 4/2002 | Bieniarz | |
| 6,844,320 B1 | 1/2005 | Garfield et al. | 514/12 |
| 7,300,664 B1 | 11/2007 | Jossifoff et al. | |
| 2002/0031513 A1 | 3/2002 | Leibovitz | 424/141.1 |
| 2003/0092691 A1 | 5/2003 | Besse et al. | |
| 2003/0099651 A1 | 5/2003 | Leibovitz | 424/145.1 |
| 2003/0113319 A1 | 6/2003 | Leibovitz | 424/141.1 |
| 2004/0266025 A1 | 12/2004 | Hickok et al. | 436/518 |
| 2005/0163771 A1 | 7/2005 | Leibovitz | 424/133.1 |
| 2005/0222105 A1 | 10/2005 | Grasset et al. | 514/177 |
| 2006/0275360 A1* | 12/2006 | Ahmed et al. | 424/451 |

FOREIGN PATENT DOCUMENTS

WO  WO 2006/042021 A2  4/2006
WO  WO 2006/128057 A2  11/2006

OTHER PUBLICATIONS

Kirn, T. Family Practice News, 2000, pp. 1-3.*
Martel et al. Journal of Applied Polymer Science, 2005, vol. 97, pp. 433-442.*
Progesterone Support in Pregnancy, 2006, pp. 1-9.*
ACOG Practice Bulletin No. 31, "Assessment of Risk Factors for Preterm Birth," *ACOG*, vol. 98, No. 4, pp. 709-716 (2001).
Alexander, J.M., et al., "Comparison of Maternal and Infant Outcomes From Primary Cesarean Delivery During the Second Compared With First Stage of Labor," *Obstet. Gynecol.*, vol. 109, No. 3, pp. 917-921 (2007).
American College of Obstetricians and Gynologists Committee Opinion No. 291, "Use of Progesterone to Reduce Preterm Birth," vol. 102, No. 5, pp. 1115-1116 (2003).
Berghella, V., et al., "Natural History of Cervical Funneling in Women at High Risk for Spontaneous Preterm Birth," *Obstet. Gynecol.*, vol. 190, No. 4, pp. 863-869 (2007).
Berghella, V., et al., "Short cervix on ultrasound: Does indomethacin prevent preterm birth?" *Am. J. Obstet. Gynecol.*, vol. 195, pp. 809-813 (2006).
Chwalisz, K. et al., "The effect of antigestagen ZK 98.299 on the uterine cervix," *Acta endocrine logica*, Program of Plenary Sessions and Advance Abstracts of Short Communications, pp. 113-114 (1987).
Cicinelli, E., et al., "Direct Transport of Progesterone From Vagina to Uterus," *Obstet. Gynecol.*, vol. 95, No. 3, pp. 403-406 (2000).
Defranco, E.A., et al., "Vaginal progesterone may reduce the risk of early preterm birth and improve neonatal outcome in women with a short cervix: results of a secondary analysis," *Ultrasound Obstet. Gynecol.*, vol. 30, 000-000 (2007).
Dodd, J.M., et al., "Prenatal administration of progesterone for preventing preterm birth (Review)," *The Cochrane Collaboration*, published by John Wiley & Sons, Ltd. (2006).
Fonseca, E. B., et al., "Progesterone and the Risk of Preterm Birth among Women with a Short Cervix," N. Engl. J. Med., vol. 357, No. 5, pp. 462-469 (2007).

(Continued)

*Primary Examiner*—Sreeni Padmanabhan
*Assistant Examiner*—Samira Jean-Louis

(57) ABSTRACT

A method for treating or preventing spontaneous preterm birth in pregnant women and improving neonatal morbidity and mortality. The method includes administering to a pregnant woman in need thereof an effective amount of progesterone sufficient to prolong gestation by minimizing the shortening or effacing of her cervix. Treatment and prophylaxis with progesterone in pregnant women having symptoms of short cervix has been clinically shown to increase neonatal health.

20 Claims, 17 Drawing Sheets

OTHER PUBLICATIONS

Gibbons, W.E., et al., "Experience with a novel vaginal progesterone preparation in a donor oocyte program," *Fertility and Sterility*, vol. 69, No. 1, pp. 96-101 (1998).
Gonik, B.,et al., "Preterm labor: Its diagnosis and treatment," *Am. J. Obstet. Gynecol.*, vol. 154, pp. 3-8 (1986).
Grimes-Dennis, J., et al., "Cervical length and prediction of preterm delivery," *Curr. Opin. Obstet Gynecol.*, vol. 19, pp. 191-195 (2007).
Hamilton, B.E., et al., "Annual Summary of Vital Statistics: 2005," *Pediatrics*, vol. 119, No. 2, pp. 345-360 (2007).
Hoenig, J.M., et al., "The Abuse of Power: The Pervasive Fallacy of Power Calculations for Data Analysis," *The American Statistician*, vol. 55, No. 1, pp. 19-24 (2001).
Iams, J.D., "Supplemental progesterone to prevent preterm birth," *Am. J. Obstet. Gynecol.*, vol. 188, p. 303 (2003).
Iams, J.D., et al., "The length of the cervix and the risk of spontaneous premature delivery," *N.E. Journ. Med.*, vol. 334, No. 9, pp. 567-572 (1996).
Iams, J.D., et al., "The Preterm Prediction Study: Recurrence risk of spontaneous preterm birth," *Am. J. Obstet Gynecol.*, vol. 178, pp. 1035-1040 (1998).
Ito, A., et al., "Suppression of interleukin 8 production by progesterone in rabbit uterine cervix," *Biochem J.*, vol. 301, pp. 183-186 (1994).
Keirse, M., "Progesterone administration in pregnancy may prevent preterm delivery," *Brit. J. Obstet. Gynocol.*, vol. 97, pp. 149-154 (1990).
Kleinstein, J., "Efficacy and tolerability of vaginal progesterone capsules (Utrogest 200) compared with progesterone gel (Crinone 8%) for luteal phase support during assisted reproduction," *Fertility and Sterility*, vol. 83, No. 6, pp. 1641-1649 (2005).
Lam, F., et al., "Evaluation of the pregnancy prolongation index (PPI) as a measure of success of obstetric interventions in the prevention of preterm birth and associated morbidities," *Am. J. Obstet. Gynecol.*, vol. 192, pp. 2047-2054 (2005).
Landon, M.B., et al., "Maternal and Perinatal Outcomes Associated with a Trial of Labor after Prior Cesarean Delivery," *N.Engl. J. Med.*, vol. 351, No. 25, pp. 2581-2589 (2004).
Lenth, R.V., "Some Practice Guidelines for Effective Sample Size Determination," *The American Statistician*, vol. 55, No. 3, pp. 187-193 (2001).
Mackenzie, R., et al., "Progesterone for the prevention of preterm birth among women at increased risk: A systematic review and meta-analysis of randomized controlled trials," *Am. J. Obstet. Gynecol.*, vol. 194, pp. 1234-1242 (2006).
Marlow, D.M., et al., "Neurologic and Developmental Disability at Six Years of Age after Extremely Preterm Birth," *N. Engl. J. Med.*, vol. 352, No. 1, pp. 9-19 (2005).
Mercer, B.M., "Preterm Premature Rupture of the Membranes," *Obstet. Gynecol.*, vol. 101, pp. 178-193 (2003).
Press Release, Society for Maternal-Fetal Medicine, "Preterm Delivery Risk Reduced by High-Dose Progesterone Treatment—March of Dimes Award Recognizes New Research," Feb. 8, 2007.
Rajabi, M.R., et al., "Immunochemical and Immunohistochemical Evidence of Estrogen-Mediated Collagenolysis as a Mechanism of Cervical Dilatation in the Guinea Pig at Parturition," *Endocrinology*, vol. 128, No. 1, pp. 371-378 (1991).
Romero, R., et al., "The preterm parturition syndrome," *BJOG*, vol. 113 (Suppl. 3), pp. 17-26 (2006).
Rouse, D.J., et al., "A Trial of 17 Alpha-Hydroxyprogesterone Caproate to Prevent Prematurity in Twins," *N. Engl. J. Med.*, vol. 357, No. 5, pp. 454-461 (2007).
Saigal, S., et al,. "Transition of Extremely Low-Birth-Weight Infants From Adolescence to Young Adulthood—Comparison with Normal Birth-Weight Controls," *JAMA*, vol. 295, No. 6, pp. 667-675 (2006).
Steer, P., "The epidemiology of preterm labour," *BJOG*, vol. 112, Supplement 1, pp. 1-3 (2005).
Thornton, J.G., "Progesterone and Preterm Labor—Still No Definite Answers," *N. Engl. J. Med.*, vol. 357, No. 5, pp. 499-501 (2007).
To, M.S., et al., "Prediction of patient-specific risk of early preterm delivery using maternal history and sonographic measurement of cervical length: a population-based prospective study," *Ultrasound Obstet Gynecol.*, vol. 27, pp. 362-367 (2006).
Toner, J.P., "The luteal phase: luteal support protocols," *Textbook of Assisted Reproductive Techniques*, pp. 639-650 (2001).
Yemini, M. et al., "Prevention of premature labor by 17α-hydroxyprogesterone caproate," *Am. J. Obstet. Gynecol.*, vol. 151, No. 6, pp. 574-577 (1985).
Eduardo B. da Fonseca, et al., "prophylactic Administration of Progesterone by Vaginal Suppository to Reduce the Incidence of Spontaneous Preterm Birth in Women at Increased Risk: A Randomized Placebo-Controlled Double-Blind Study," American Journ., of OBYN, St. Louis, MO, Feb. 2003, vol. 188, No. 2, pp. 419-424.
Jay D. Iams, et al., Cervical Competence As A Continuum: A Study of Ultrasonographic Cervical Length and Obstetric Performance, American Jorn. of OBYN, Apr. 1995, vol. 172, No. 4, Part 1, pp. 1097-1103.
Orion Rust, et al., "A Randomized Trial of Cerclage Versus 17-Hydroxyprogesterone (17p) for the Treatment of Short Cervix," American Journ. of OBGYN, vol. 195, No. 6, Dec. 2006, p. S112.
T.K.A. B. Eskes, "Progesterone or Isoxsuprine in Premature Labour," Gull. Soc. Roy. Belg. Gynec., Obstet., 1964, vol. 34, No. 1, pp. 9-13.
Paul J. Meis for the Society for Maternal-Fetal Medicine, "17-Hydroxyprogesterone for the Prevention of Preterm Delivery," May 2005, vol. 105, No. 5, pp. 1128-1135.
"Progesterone for Prevention of Preterm Births in Women with Short Cervix: Randomized Controlled Trial," Clinical Trials.gov, Jan. 2007 (URL: http://clinicaltrials.gov/show/record/NCT00422526?TERM=PROGESTERONE+AND+PREVENTION + AND+PRETERM&rank=3).
ACOG Committee Opinion, "Use of Progesterone to Reduce Preterm Birth," International Journ. of Gynecology & Obstetrics, 2004, pp. 93 and 94.
American Journal of OB & GYN, Dec. 2006, vol. 195, No. 6, Supplemental p. S5 (Abstract).
International Search Report dated Dec. 11, 2008 (PCT/GB08/00397).
Dodd, et al., "Progesterone Supplementation for Preventing Preterm Birth: A systematic review and meta-analysis," Acta Obstetricia et Gynecologica Scandinavica, vol. 84, pp. 526-533 (2005).
Meis, et al., "Prevention of Recuurent Preterm Delivery by 17 Alpha-Hydroxyprogesterone Caproate," New England Journal of Medicine, vol. 348, No. 24, pp. 2379-2385, Jun. 13, 2003.
Facchinetti, et al., "17 Alpha Hydroxy-Progesterone Caproate (17P) Treatment Reduces Cervical Shortening Inhibiting Cervical Interleukin-1 Secretion," American Journal of Obstetrics and Gynecology, vol. 195, No. 6, Dec. 2006, p. S5.
Rust, et al., "A randomized trial of cerclage versus 17-hydroxyprogesterone (17p) for the treatment of short cervix," American Journal of Obstetrics and Gynecology, vol. 195, No. 6, Dec. 2006, p. S112.
Anonymous: "Progesterone for prevention of preterm births in women with short cervix: randomized controlled trial, Study NCT00422526," Jan., 2007, downloaded from www.clinicaltrials.gov.
Fonseca Eduardo, et al., "Progesterone and the risk of preterm birth among women with a short cervix," New England Journal of Medicine, vol. 357, No. 5, Aug. 2007, pp. 462-469.
Coomarasamy, et al. "Progesterone for the prevention of preterm birth: A critical evaluation of evidence," European Journal of Obstetrics & Gynecology and Reproductive Biology, vol. 129 pp. 111-118 (2006);.
Eduardo B. da Fonseca, et al., "Prophylactic Administration of Progesterone by Vaginal Suppository to Reduce the Incidence of Spontaneous Preterm Birth in Women at Increased Risk: A Randomized Placebo-Controlled Double-Blind Study," American Journ., of OBYN, St. Louis, MO, Feb. 2003, vol. 188, No. 2, pp. 419-424.
"Use of Progesterone to Reduce Preterm Birth," The American College of Obstetricians, No. 4, vol. 112, Oct. 2008, pp. 963-965.
"Cervical Insufficiency," The American College of Obstetricians, vol. 102, No. 5, Nov. 2003, pp. 1091-1099.

* cited by examiner

Demographics and Pre-treatment Subject Characteristics

| | Descriptive Statistic | Placebo (N = 302) | Prochieve (N = 309) | Total (N = 611) |
|---|---|---|---|---|
| Age (Years) | n | 302 | 308 | 610 |
| | Mean | 27.3 | 27.1 | 27.2 |
| | Std. Dev. | 5.60 | 5.82 | 5.71 |
| | Median | 26.5 | 25.9 | 26.2 |
| | Min – Max | 17.9 – 40.8 | 16.1 – 44.2 | 16.1 – 44.2 |
| Race | | | | |
| Caucasian | n (%) | 99 (32.8%) | 111 (35.9%) | 210 (34.4%) |
| African-American | n (%) | 85 (28.1%) | 76 (24.6%) | 161 (26.4%) |
| Hispanic | n (%) | 14 (4.6%) | 22 (7.1%) | 36 (5.9%) |
| Asian/Pacific Islander | n (%) | 60 (19.9%) | 55 (17.8%) | 115 (18.8%) |
| Native American | n (%) | 1 (0.3%) | 0 | 1 (0.2%) |
| Other | n (%) | 43 (14.2%) | 45 (14.6%) | 88 (14.4%) |
| Cervical Length (cm) | n | 295 | 305 | 600 |
| | Mean | 3.7 | 3.7 | 3.7 |
| | Std. Dev. | 0.90 | 0.72 | 0.81 |
| | Median | 3.6 | 3.7 | 3.6 |
| | Min – Max | 1.1 – 7.9 | 2.0 – 6.4 | 1.1 – 7.9 |
| Gestational Age First Dose (1) | | | | |
| < 18 0/7 Weeks | n (%) | 21 (7.0%) | 25 (8.1%) | 46 (7.9%) |
| 18 0/7 Weeks to <= 18 6/7 Weeks | n (%) | 85 (28.1%) | 85 (27.5%) | 170 (27.8%) |
| 19 0/7 Weeks to <= 19 6/7 Weeks | n (%) | 66 (21.9%) | 56 (18.1%) | 122 (20.0%) |
| 20 0/7 Weeks to <= 20 6/7 Weeks | n (%) | 39 (12.9%) | 53 (17.2%) | 92 (15.1%) |
| 21 0/7 Weeks to <= 21 6/7 Weeks | n (%) | 34 (11.3%) | 41 (13.3%) | 75 (12.3%) |
| >= 22 0/7 Weeks | n (%) | 57 (18.9%) | 49 (15.9%) | 106 (17.3%) |

(1) Gestational age at first dose is calculated based on the accepted estimated data of confinement.

Fig. 1

Baseline demographic and obstetric characteristics of women with a short cervix (<28 mm)

| | Progesterone (n = 19) | Placebo (n = 27) | Total (n = 46) | P value |
|---|---|---|---|---|
| Maternal age (years), mean (SD) | 27.4 (4.9) | 25.4 (4.8) | 26.2 (4.9) | 0.18 |
| Race/Ethnicity, n (%) | | | | |
| Caucasian | 9 (47.4) | 10 (37) | 19 (41.3) | 0.55 |
| African-American | 3 (15.8) | 11 (40.7) | 14 (30.4) | 0.10 |
| Hispanic | 1 (5.3) | 0 | 1 (2.2) | 0.40 |
| Asian/Pacific Islander | 0 | 4 (14.8) | 4 (8.7) | 0.13 |
| Other | 6 (31.6) | 2 (7.4) | 8 (17.4) | 0.05 |
| Body mass index (BMI), mean (SD) | 28.5 (8.3) | 26.9 (6.7) | 27.6 (7.3) | 0.52 |
| No. of deliveries, mean (SD) | 1.1 (0.8) | 1.6 (1.1) | 1.3 (1.0) | 0.09 |
| No. of prior preterm births, mean (SD) | 1.2 (0.5) | 1.4 (0.8) | 1.3 (0.7) | 0.26 |
| >1 prior preterm birth, n (%) | 7 (37) | 5 (19) | 12 (26) | 0.80 |
| Prior cervical surgery, n (%) | 3 (16) | 6 (22) | 9 (20) | 0.70 |
| No. of prior spontaneous abortions, mean (SD) | 0.8 (1.4) | 0.4 (0.7) | 0.6 (1.1) | 0.22 |
| Gestational age at randomization (weeks), mean (SD) | 19.9 (2.1) | 20.1 (3.3) | 20.0 (2.8) | 0.98 |

Fig. 3

Cervical Length at Week 28.

| Cervical Length (cm) | Placebo (n=302) | Prochieve (N=309) | Change from Screening Placebo | Change from Screening Prochieve | Difference | 95% Confidence Interval |
|---|---|---|---|---|---|---|
| Week 28 | | | | | | |
| n | 280 | 275 | 274 | 273 | | |
| Mean | 3.1 | 3.3 | -0.6 | -0.5 | -0.16 | (-0.31, -0.01) |
| Std. Dev. | 0.93 | 0.87 | 0.90 | 0.87 | | |
| Median | 3.1 | 3.2 | -0.5 | -0.3 | | |
| Min – Max | 0.5 – 5.9 | 0.6 – 5.8 | -3.6 – 1.9 | -3.9 – 1.7 | | |

| Analysis of Covariance (ANCOVA) | | |
|---|---|---|
| Source | df | p-value |
| Investigator effect | 5 | 0.349 |
| Gestational Age of the Previous Preterm Delivery (wks) | 1 | 0.344 |
| Subject's age (yr) | 1 | 0.832 |
| Cervical Length at Screening (cm) | 1 | 0.015 |
| Body Mass Index (kg/m**2) | 1 | <0.001 |
| Race | 1 | 0.960 |
| | 3 | 0.123 |
| Treatment Group | 1 | 0.020 |

Week 28 Change from Screening Adjusted Means (LSmeans):  Placebo = -0.61   Prochieve = -0.44   -0.16   (-0.30, -0.03)

P-Value for Overall Test of the Raw Means: 0.038

NOTE: P-value for overall test of raw means based on t-test.

Fig. 4

Preterm birth outcomes in women with a cervical length < 28 mm at enrollment

| | Progesterone (n = 19) | Placebo (n = 27) | P value |
|---|---|---|---|
| Gestational age at birth (weeks), mean (SD) | 36.3 (2.4) | 34.6 (4.6) | 0.160 |
| Preterm birth, n (%) | | | |
| <37 weeks | 8 (42.1) | 16 (59.3) | 0.370 |
| ≤35 weeks | 7 (36.8) | 13 (48.1) | 0.551 |
| ≤32 weeks* | 0 | 8 (29.6)† | 0.014‡ |
| ≤28 weeks | 0 | 3 (11.1) | 0.257 |
| Cervical length at enrollment (mm) | | | |
| mean (SD) | 24 (0.2) | 22 (0.5) | 0.07 |
| median (range) | 25 (19-27) | 25 (11-27) | |
| Cervical length at 28 weeks (mm), mean (SD) | 25 (0.8) | 22 (0.8) | 0.27 |
| Change in cervical length (mm), mean (SD) | 2 (0.9) | 0 (0.9) | 0.70 |
| Admission for preterm labor, n (%) | 6 (31.6) | 7 (25.9) | 1.0 |
| Latency period to delivery after tocolysis for preterm labor (days), mean (SD) | 42.7 (52.3) | 10.0 (18.0) | 0.287 |
| Compliance§, % (SD) | 93.9 (9.77) | 94.7 (13.03) | |

Fig. 11

Neonatal outcomes in women with a cervical length < 28 mm at enrollment

| | Progesterone (n = 19) | Placebo (n = 27) | P value |
|---|---|---|---|
| Birth weight (g), mean (SD) | 2726 (645) | 2290 (937) | 0.1 |
| No. of hospital days, mean (SD) | 5.8 (9) | 18.2 (25.5) | 0.055 |
| NICU admission, n (%) | 3 (15.8) | 14 (51.9) | 0.016 |
| No. of days in NICU for admissions, mean (SD) | 1.1 (2.7) | 16.5 (24.9) | 0.013 |
| Respiratory distress syndrome, n (%) | 1 (5.3) | 8 (29.6) | 0.060 |
| Intraventricular hemorrhage, n (%) | | | |
| Grade 1 | 0 | 2 (7.4) | 0.5 |
| Grade 2 | 0 | 0 | |
| Grade 3 | 0 | 0 | |
| Grade 4 | 0 | 0 | |
| Necrotizing enterocolitis, n (%) | | | |
| Surgical | 0 | 0 | |
| Clinical | 0 | 1 (3.7) | 1.0 |
| Proven sepsis, n (%) | 1 (5.3) | 3 (11.1) | 1.0 |
| Neonatal death, n (%) | 0 | 1 (3.7) | 1.0 |

Fig. 12

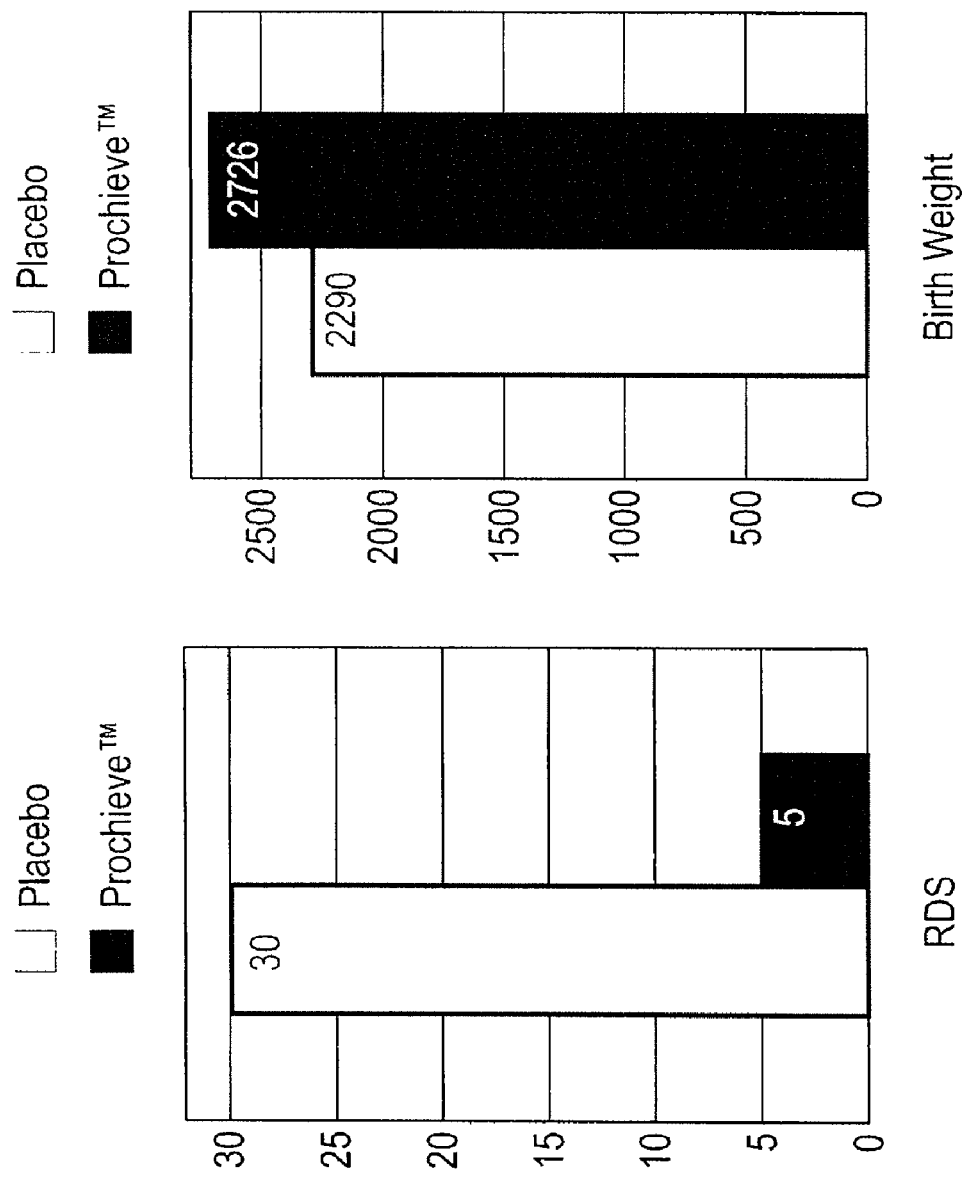

PROGESTERONE FOR THE TREATMENT OR PREVENTION OF SPONTANEOUS PRETERM BIRTH

CROSS-REFERENCE TO PRIOR APPLICATIONS

The present application is a continuation of U.S. patent application Ser. No. 12/024,756, which was filed on Feb. 1, 2008, entitled "PROGESTERONE FOR THE TREATMENT OR PREVENTION OF SPONTANEOUS PRETERM BIRTH," which is hereby incorporated by reference in its entirety; this application also claims the benefit of U.S. Provisional Application No. 60/888,480, which was filed on Feb. 6, 2007, and U.S. Provisional Application No. 60/973,667, which was filed on Sep. 19, 2007, the disclosures of which are fully incorporated herein by reference.

FIELD OF THE INVENTION

The present invention relates to a method for treating or preventing spontaneous preterm birth in pregnant women while improving neonatal health. More particularly, the invention relates to a method of treating or preventing the onset of preterm labor leading to preterm birth by administering to a pregnant woman an amount of progesterone that is sufficient to prolong gestation by delaying the shortening or effacing of her cervix. Additionally, the invention relates to a method of treating or preventing the onset of preterm labor while decreasing neonatal mortality and/or morbidity by administering to a pregnant woman symptomatic of a short cervix an effective amount of progesterone to delay labor and to decrease neonatal mortality and/or morbidity.

BACKGROUND OF THE INVENTION

It is generally known that pregnant women who experience spontaneous preterm birth (PTB) begin with preterm labor (also interchangeably referred to herein as "premature labor") and start having regular contractions that cause their cervix to start to open or thin out (called dilation and effacement) and soften before they reach about 37 weeks of gestation. If a woman delivers a baby before 37 weeks, it is typically and conventionally called a preterm birth and the baby is considered premature.

Preterm birth remains one of the most serious problems in obstetrics, with enormous impact on infants, their families, and our society. According to a recent study published by the Institute of Medicine, the incidence of preterm birth has grown 33% since 1981, and each year approximately 500,000 women deliver prematurely in the U.S. alone resulting in a $26 billion annual cost of premature birth to our nation's healthcare system. It has recently been reported that preterm births occur in 15% of pregnancies in the developed world and 12.7% of all births in the United States in 2006 and 12.4% of all births in the United States in 2004. See, e.g., *Use of progesterone to reduce preterm birth*, American College of Obstetricians and Gynecologists Committee Opinion No. 291, Vol. 102, No. 5, November 2003, pages 1115-1116; Hamilton, B. E., *Annal Summary of Vital Statistics: 2005*, Pediatrics, Vol. 119, No. 2, February 2007, pages 345-360.

It is believed that a preterm birth prior to 32 weeks of gestation represents an extremely high risk of morbidity and mortality. Additionally, a preterm birth between 32 and 36 weeks of gestation has been found to be particularly alarming as having a great number of at risk infants. Preterm delivery accounts for 60-70% of infant mortality, and is a leading cause of health care expenditures in both the perinatal period and throughout life for infant survivors. Recent advances in modern obstetric and neonatal care have led to improved infant survival, however, 55% of newborns with an extremely low birth weight (<1000 g) or delivered very premature (<28 weeks) who survive to middle childhood show evidence of clinically significant cognitive, educational, and behavioral impairment.

Approximately 20%-30% of preterm births are the result of a physician's decision to bring about delivery for maternal or fetal indications. The remainder of preterm deliveries is spontaneous, usually following the onset of premature labor or rupture of the membranes. Several risk factors for preterm labor have been identified including: multi-fetal gestation, maternal stress, systemic and intrauterine infection, race, and socioeconomic status. The Preterm Prediction Study found that a history of prior spontaneous preterm delivery was a strong predictor of subsequent preterm delivery with a prior delivery at 23-27 weeks giving rise to an 11-fold increase in the risk. Unfortunately, however, risk assessment methods using only historical risk factors have an unacceptably low sensitivity and poor predictive value. Supplementing historical-based risk assessment with technology, specifically an ultrasonographic assessment of the cervix, adds improved sensitivity and specificity. Ultrasound identification of cervical shortening is correlated with a logarithmic increase in the risk of preterm delivery. See Jams et al, *The length of the cervix and the risk of spontaneous premature delivery*, N. Engl. J. Med. 1996; 334: 567-572.

Of the surviving premature infants, many are afflicted with lifelong difficulties such as cerebral palsy, mental retardation, chronic lung disease, hearing and vision deficits, and learning disabilities. The more mature a child is at birth, the more likely he or she is to survive and the less likely he or she is to have related health problems. Premature babies born between 34 and 37 weeks are generally relatively healthy. If a woman goes into labor before 34 weeks, however, the risks of adverse health effects and/or medical complications increase.

It is generally known that the length of a woman's cervix is a good indication of whether a pregnant woman will experience preterm labor and preterm birth. Physicians routinely check the length of a woman's cervix at the first prenatal visit, so that they can monitor changes in cervical length as the pregnancy progresses. If a woman's cervix gets shorter at midpregnancy, it means that the cervix is beginning to efface (thin out), and it is a good indication that the woman is at higher risk for preterm delivery.

Cervical shortening, and to some degree such characteristics as previous preterm birth history, age, ethnicity, body mass index (BMI) and cervical surgery, are conventionally known risk factors related to preterm birth. Data support an inverse relationship between cervical length and preterm delivery. In a prospective study of 2915 women that investigated the relationship between short cervical length and preterm delivery, researchers found that even a small decrease in cervical length between the $24^{th}$ and $28^{th}$ weeks of gestation was associated with an increased risk of preterm birth (RR 2.03; 95% CI, 1.28-3.22). See Iams et al, *The length of the cervix and the risk of spontaneous premature delivery*, N. Engl. J. Med. 1996; 334: 567-572. At 24 weeks, when compared with women whose cervical length was above the $75^{th}$ percentile of normal, women who had a cervical length in the $25^{th}$ percentile (<3.0 cm) had a relative risk of preterm delivery of 3.79 (95% CI, 2.32-6.19); those in the $10^{th}$ percentile (<2.6 cm) had a relative risk of 6.19 (95% CI, 3.84-9.97); those in the $5^{th}$ percentile (<2.2 cm) had a relative risk of 9.49 (95% CI, 5.95 to 15.15); and those in the $1^{st}$ percentile (<1.3 cm) had a relative risk of 13.99 (95% cm 7.89 to 24.78). Id.

Other studies have determined that monitoring cervical length may aid in the identification of women at an increased risk for recurrent preterm birth. See Spong, C., *Prediction and prevention of recurrent spontaneous preterm birth*, American College of Obstetricians and Gynecologists, Vol. 110, No. 2, Part 1, August 2007, pages 407-408.

There is currently no approved therapy for preventing preterm births in the United States. See Institute of Medicine Report on Preterm Birth, 2006. Existing medical practice for preventive treatments regarding a short cervix early in gestation involves mechanical/surgical treatments. For example, cervical cerclage is a surgical procedure where the cervix is sewn or stitched closed, thus physically preventing the cervix from prematurely shortening or thinning out. The stitches are then removed, typically at about week 37, to allow normal dilation of the cervix during labor. Unfortunately, typical adverse effects associated with cervical cerclage procedures include risk of premature contractions, cervical dystocia (inability of the cervix to dilate normally during labor), cervical infections, and other risks generally associated with surgical procedures. In addition, there is controversy about the effectiveness of cerclage in the treatment of a short cervix. Several recent studies suggest this surgical treatment is no better than placebo. Although cervical length, specifically cervical shortening is known to be correlated to preterm birth, no non-surgical intervention is presently known to be efficacious. See Spong, C., pages 407-408. That is, there is currently no accepted medical treatment for the risk factor for preterm labor and birth known as "short cervix".

Progesterone administration has been advocated for the prevention of preterm birth in certain women considered to be at high risk, although the primary focus has been on patients with a prior history of preterm birth. The efficacy of vaginally administered progesterone to prevent preterm birth in women at especially high risk of preterm delivery, particularly women experiencing cervical shortening, is far from concrete and is largely unknown. O'Brien et al., for example, have determined that prophylactic treatment with vaginal progesterone gel does not effectively reduce the frequency of recurrent preterm birth in high risk women selected by a history of spontaneous preterm birth. As provided by the Committee on Obstetric Practice of the American College of Obstetricians and Gynecologists in the publication, *Use of Progesterone to Reduce Preterm Birth*, American College of Obstetricians and Gynecologists Committee Opinion No. 291, Vol. 102, No. 5, November 2003, pages 1115-1116, the ideal progesterone formulation is unknown, however.

The use of progesterone to treat all women at risk for preterm birth does not have unqualified support at present. Several authors have expressed the need for adequately designed, randomized trials in larger populations to identify the ideal progesterone formulation and dosage, and to demonstrate a decline in preterm births before 37 weeks and a reduction in perinatal morbidity and mortality. See, e.g., Dodd et al, *Prenatal administration of progesterone for preventing preterm birth*, Cochrane Database Syst Rev 2006.

While there is much debate regarding the use of progesterone regarding birth, specifically regarding the period of gestation, there is little, if any, conventional art analyzing effects to neonatal populations based on treatments for preventing preterm birth. Meta-analysis of randomized trials involving women revealed that there may be a reduction in the risk of preterm birth less than 37 weeks and 34 weeks. Dodd, J. M. et al, *Prenatal administration of progesterone for preventing preterm birth (Review)*, The Cochrane collaboration, John Wiley Sons, Ltd, 2006, pages 1-36. Importantly, however, there was no statistically significant difference in the occurrence of perinatal death between women administered progesterone and those administered placebo. Dodd, J. M. et al, pages 4-5. In fact, no differences were reported regarding neonatal outcomes between the placebo and progesterone groups. Dodd, J. M. et al, pages 4-5; Mackenzie, R. et al., *Progesterone for the prevention of preterm birth among women at increased risk. A systematic review and meta-analysis of randomized controlled trials*, Journal of Obstetrics and Gynecology, 194, 2006, pages 1234-42.

One study provided information regarding pregnancy prolongation and the morbidity of the child. Lam, F. et al., *Evaluation of the pregnancy prolongation index (PPI) as a measure of success of obstetric interventions in the prevention of preterm birth and associated morbidities*, Journal of Obstetrics and Gynecology, 192, 2005, 2047-54. This study, however, provided no comparative experimental data between treatment groups and control groups. Moreover, this study did not relate to use of progesterone for treatment or prophylaxis of preterm birth. Ultimately, this study was limited to examining neonatal health simply as a function of gestational age at delivery rather than as a consequence of a treating/prophylactic agent.

Thus, there is a need for a method of treating or preventing the onset of preterm labor and resulting preterm birth in pregnant women, particularly for women having a short cervix, without the adverse health effects that are typically associated with currently known methods. Moreover, beyond just focusing on the health of the mother giving birth, there needs to be a strong focus on, and intervention for, improving neonatal outcome. That is, preterm birth is associated with high perinatal morbidity and mortality; and suppression of premature labor has not conventionally been associated with improved infant outcomes. The conventional art does not show any direct health benefits to the neonate. Therefore, there is a need in the art for treatment and/or prophylaxis to improve natal, particularly neonatal, health for births occurring preterm.

SUMMARY OF THE INVENTION

The present invention is directed to a method for treating or preventing the onset of preterm labor and subsequent preterm birth in pregnant women. In a preferred embodiment, the method includes administering to a pregnant woman in need thereof an effective amount of progesterone that is sufficient to prolong gestation by delaying the shortening or effacing of the cervix. Preferably, the progesterone is administered as a vaginal gel, as a vaginal suppository, as vaginal cream, or a vaginal solid dosage form (such as a tablet), or through means of a delivery device inserted into the vagina, such as a cervical ring or other devices as generally known in the art.

The present invention provides a method of improving neonatal health, i.e., morbidity and/or mortality, in births by women with short cervical length in mid-pregnancy. The method of improving neonatal morbidity and mortality comprising administering to a pregnant woman with a short or effaced cervix in need thereof an effective amount of progesterone sufficient to prolong gestation. In some embodiments, neonates born to women receiving progesterone treatment and/or prophylaxis are characterized by decreased neonatal morbidity and mortality, decreased number of neonatal intensive care unit (NICU) Days, decreased likelihood of admission into the NICU, or a combination thereof, as compared to babies born to mothers not provided an effective amount progesterone during gestation. In preferred embodiments, between about 45 mg and 800 mg of progesterone, either natural or synthetic or a derivative thereof, is administered as a vaginal gel. In yet additional embodiments, the progesterone is administered daily beginning about the 18th to 22nd week of gestation until about the 37th week of gestation, for preferably about 14 to 19 weeks.

In still other embodiments of the present invention, the progesterone is administered to a pregnant woman whose cervix has a length greater than about 1.0 cm and more preferably greater than 1.5 cm, wherein the progesterone is administered to a pregnant woman whose cervix has a length between about 1.0 cm and 8.0 cm. In variations, the length of the cervix in women who are administered progesterone is less than or equal to about 3.0 cm, preferably less than 2.8 cm and even more preferably less than 2.5 cm.

In the embodiments of the present invention, the progesterone administered can be progesterone molecule (from any source, including natural or synthetic) or progesterone metabolites (from any source, including natural or synthetic), or any other progestin. Progesterone itself is preferred, although other progestins may be used. Where synthetic progestin is used, preferably, the synthetic progesterone is selected from a group consisting of derivatives of progesterone or of testosterone or derivatives of other molecules with progestogenic activity. Such progestins include, but are not limited to 17-alpha-hydroxyprogesterone caproate, medroxyprogesterone acetate, norethindrone, norethindrone acetate, norethindrone enanthate, desogestrel, levonorgestrel, lynestrenol, ethynodiol diacetate, norgestrel, norgestimate, norethynodrel, gestodene, drospirenone, trimegestone, levodesogestrel, gestodyne, nesterone, etonogestrel, and derivatives from 19-nor-testosterone. In a preferred embodiment, the progesterone includes either of the natural progestins, progesterone or 17-alpha-hydroxyprogesterone. Some progestins can be delivered vaginally, some by intramuscular injection, some by oral administration, and some by rectal administration, although other routes of administration can be used as known in the art. In a preferred embodiment, the progesterone is administered via a drug delivery system that comprises progesterone, a water-soluble, water-swellable cross-linked polycarboxylic acid polymer, and at least one adjuvant.

In a preferred embodiment, the progesterone is administered daily via the vaginal route. However, the administration can be as infrequent as weekly or as often as 4 times daily, depending on the characteristics of the progestin and the progestin formulation. Preferably, the progesterone is administered beginning about the 18th to 22nd week of gestation until about the 37th week of gestation, or for approximately 14 to 19 weeks, depending on the gestational age at the beginning of treatment and the date of delivery. In another embodiment, the progesterone is administered beginning about the 16th week of gestation until about the 37th week of gestation, or for approximately 21 weeks. In still other embodiments, the progesterone is administered beginning about the time of a positive pregnancy test until about the 37th week of gestation, or beginning about the 2nd to 4th week of gestation, for approximately 33 to 35 weeks.

The amount of progesterone administered is preferably between about 45 mg and 800 mg, and more preferably between about 90 mg and 250 mg, based on the progestin effect of natural progesterone administered vaginally, but may be more or less depending on the potency of the progestin and the route of administration. The progesterone is preferably administered to a pregnant woman beginning as early as the onset of gestation and whose cervix has a length greater than about 1.0 cm. More preferably, the progesterone is administered to a pregnant woman beginning as early as the onset of gestation and whose cervix has a length is at least about 1.0 cm and at most about 8.0 cm, and even more preferably, the progesterone is administered to a pregnant woman whose cervix has a length less than or equal to 2.5 cm or 3.0 cm.

Another embodiment of the present invention is to provide improved methods of treating or preventing the onset of preterm labor and premature birth by administering to a pregnant woman an amount of progesterone that is sufficient to minimize or delay the shortening or effacing of her cervix, and possibly softening and dilating.

BRIEF DESCRIPTION OF THE DRAWINGS

Other features and advantages of the invention will become apparent from the description that will now be given, with reference to the appended Figures, which show, by way of example but implying no limitation, possible embodiments of the invention.

FIG. 1 is a table that includes baseline data for participants in a study that compared the efficacy of progesterone in the treatment of preterm births in placebo and treatment groups, in accordance with one embodiment of the invention;

FIG. 3 is a table of data for participants with a short cervix of less than 2.8 cm, according to one embodiment of the invention;

FIG. 4 is a table that includes cervical length data at Week 28 for participants in the placebo and treatment groups, according to one embodiment of the invention;

FIG. 11 is a table summarizing preterm birth outcomes in study participants with a cervical length of less than 2.8 cm at enrollment, in accordance with one embodiment of the invention, FIG. 12 is a table summarizing neonatal outcomes in participants with a cervical length of less than 2.8 cm at baseline, according to one embodiment of the invention;

FIGS. 14a-e present graphs depicting infant outcomes in placebo and treatment patients with a baseline cervical length $\leq$2.8 cm, in accordance with one embodiment of the present invention.

DETAILED DESCRIPTION OF THE PREFERRED EMBODIMENTS

Figure 2:
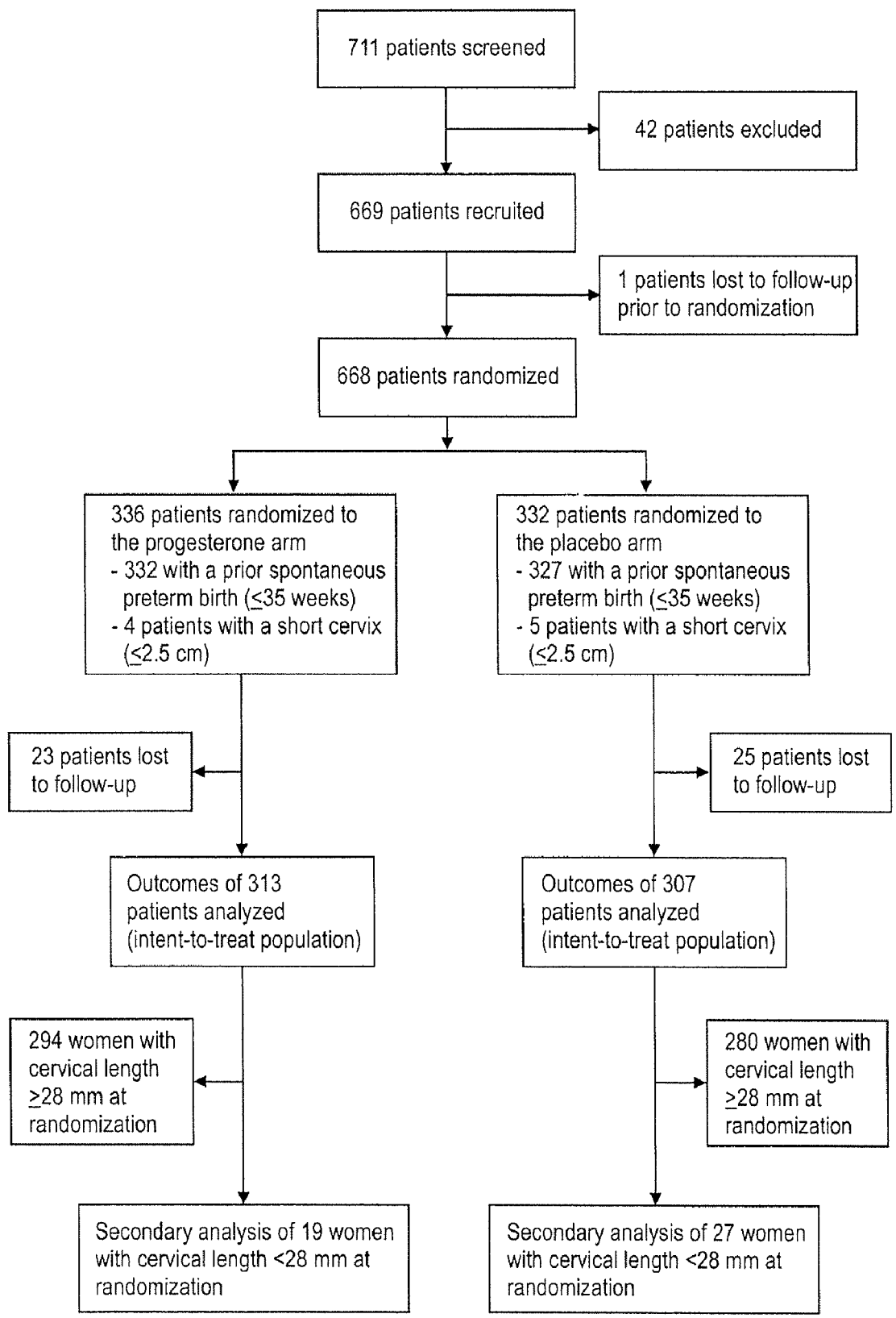
FIG. 2 is a table illustrating the trial profile of participants, according to one embodiment of the invention.

It is generally unknown in the field of obstetrics to administer progesterone to a pregnant woman with a short or effaced cervix for the purpose of affecting cervical dilation and effacement in order to treat or prevent the onset of preterm labor and premature birth. In particular, and to the best of our knowledge, there is no literature or other publications that teach or suggest that progesterone can be administered to a pregnant woman with a short cervix to prolong gestation by minimizing the shortening or effacing of the cervix, and possibly the softening and dilation.

The present invention is directed to improving neonatal health by administering an effective amount of progesterone or derivative thereof to pregnant women having short or effaced cervixes. In preferred embodiments, the use of progesterone decreases the morbidity and/or mortality of neonates born to pregnant women symptomatic of a shortened cervical length. In some variations, neonates, in whom the mother was treated with progesterone, exhibit at least one of: 1) a decrease in neonatal intensive care unit ("NICU") Days and 2) fewer percentage proportion of admission to the NICU, (i.e., a reduction in percentage of babies admitted in the NICU). The neonates born to women being administered progesterone during pregnancy also exhibit lower incidences of neonatal disease and disorders, such as respiratory distress syndrome (RDS), intraventricular haemorrhage, necrotizing entercolitis, sepsis, and death, as compared to neonates in which the mother was not administered progesterone during pregnancy. This evidence is indicative of the decreased morbidity rate and shows that fewer babies are getting sick by treatment and/or prophylaxis of the pregnant mother having short cervix symptoms with progesterone. In accordance with this invention, treatment and prophylaxis of mothers exhibiting short cervix symptoms increases the clinical health of the resulting neonate and decreases the frequency of births on or before 37 weeks of gestation.

Embodiments of the present invention suggest that the use of progesterone in patients with short cervix produces a significant reduction in preterm birth (PTB) of less than or equal to 32 weeks of gestation and/or a significant improvement in selected infant outcomes. Additionally, embodiments suggest that women have a short cervical length, preferably less than 3.0 cm, and more preferably less than 2.8 cm, benefited from progesterone therapy as a PTB intervention strategy.

As used herein, the term "preterm" generally describes human gestation resulting in birth prior to 37 weeks. Accordingly, "preterm" covers births occurring less than 35 weeks or less than or equal to 32 weeks of gestation. Additionally, another definition of preterm labor includes dilation and/or effacement of the cervix, which is detected by digital examination, associated with persistent uterine contractions before 37 weeks of gestation. In some embodiments as discussed herein, preterm labor was defined as 6 or more uterine contractions per hour accompanied by documented cervical change, cervical dilation greater than 2 cm, cervical effacement greater than 80%, or documented change in cervical effacement greater than 50%.

As used herein, short cervix describes a cervical length from greater than 1.0 to 3.5 cm, preferably from greater than 1.0 to 3.0 cm, more preferably from greater than 1.0 to 2.5 cm, and even more preferably greater than 1.0 to 2.0 cm. A cervix that is less than 1.0 cm is commonly described as an "ultra-short cervix" and is clinically distinguishable from "short cervix." How to identify and clinically diagnose pregnant women having short cervix would be understood by one skilled in the art, and may include such methods as sonographic examination and clinical examination, for example.

As used herein, neonatal encompasses children about 6 months of age or less, preferably about 3 months of age or less, more preferably about 2 months of age or less, and even more preferably about 1 month of age or less. In certain embodiments, neonatal is used to encompass perinatal, preferably the period after birth.

As used herein, neonatal outcome (interchangeably referred to herein as "neonatal health") is measured by mortality and morbidity incidences, prevalence, and clinical states. For example, health may be directly correlated to infant weight. Health may also be inversely related to incidence of special care admission (i.e., NICU) at birth, length of neonatal hospital stay at birth, incidence of RSD, incidence of intraventricular haemorrhage, incidence of necrotizing enterocolitis, incidence of sepsis, and incidence of neonatal death. Other measures of morbidity may be used by those skilled in the art.

The term "pharmaceutically effective amount" (or interchangeably referred to herein as "an effective amount") has its usual meaning in the art, i.e., an amount of a pharmaceutical that is capable of inducing an in vivo and/or clinical response that facilitates management, prophylaxis, or therapy. This term can encompass therapeutic or prophylactic effective amounts, or both. As used herein, the term "suitable" means fit for mammalian, preferably human, use and for the pharmaceutical purposes disclosed herein.

The term "treatment" or "treating" means any treatment of a disease or disorder in a mammal, including: preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms. In some embodiments, the term "treatment" or "treating" includes ameliorating the symptoms of, curing or healing, and preventing the development of a given disease.

The term "prophylaxis" is intended as an element of "treatment" to encompass both "preventing" and "suppressing," as defined herein. It will be understood by those skilled in the art that in human medicine it is not always possible to distinguish between "preventing" and "suppressing" since the ultimate inductive event or events may be unknown, latent, or the patient is not ascertained until well after the occurrence of the event or events.

Figure 5A:
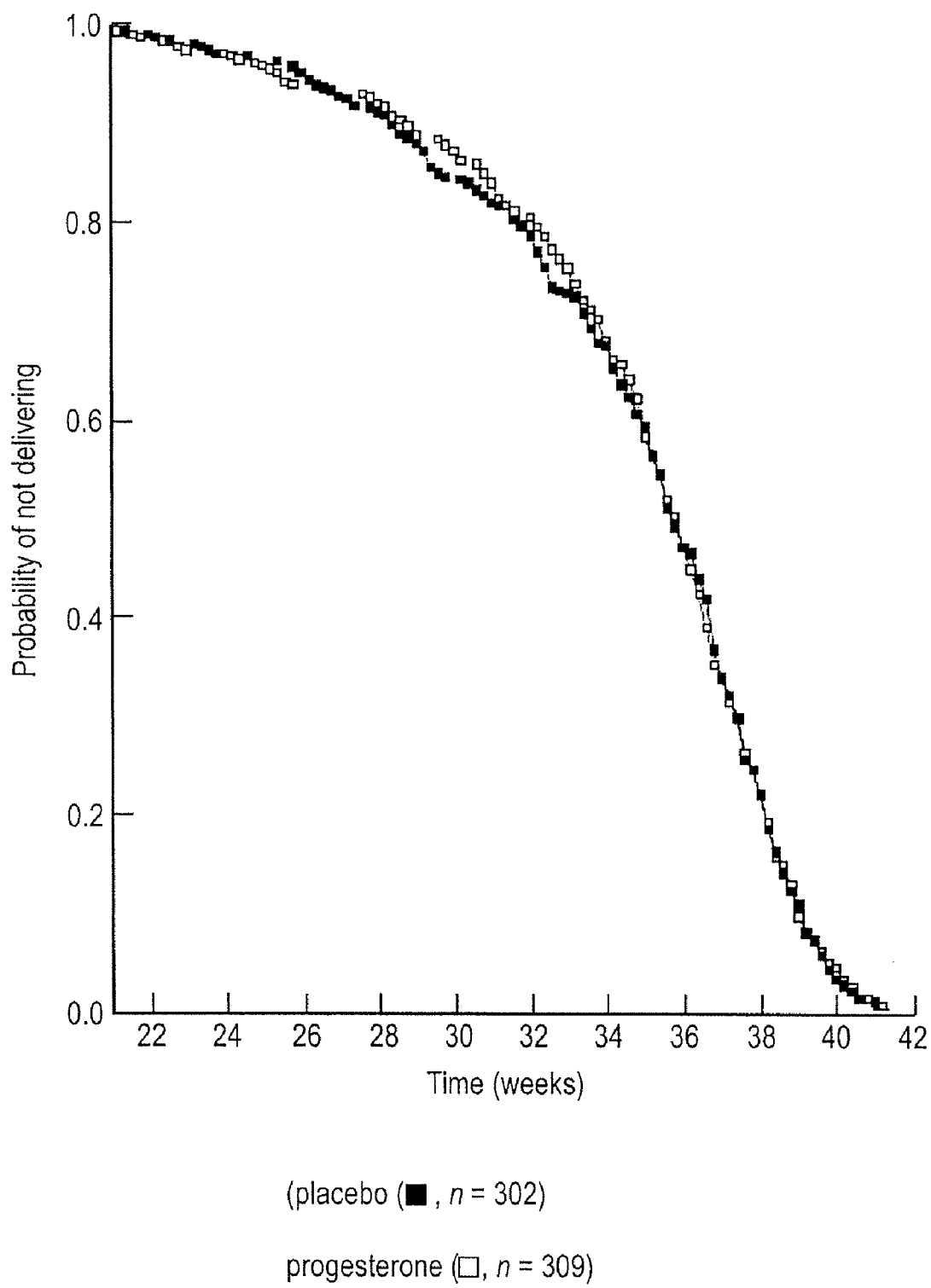
FIGS. 5a and 5b depict a delivery time curve for participants in the placebo and progesterone treatment groups, according to an embodiment of the invention.
Figure 5B:
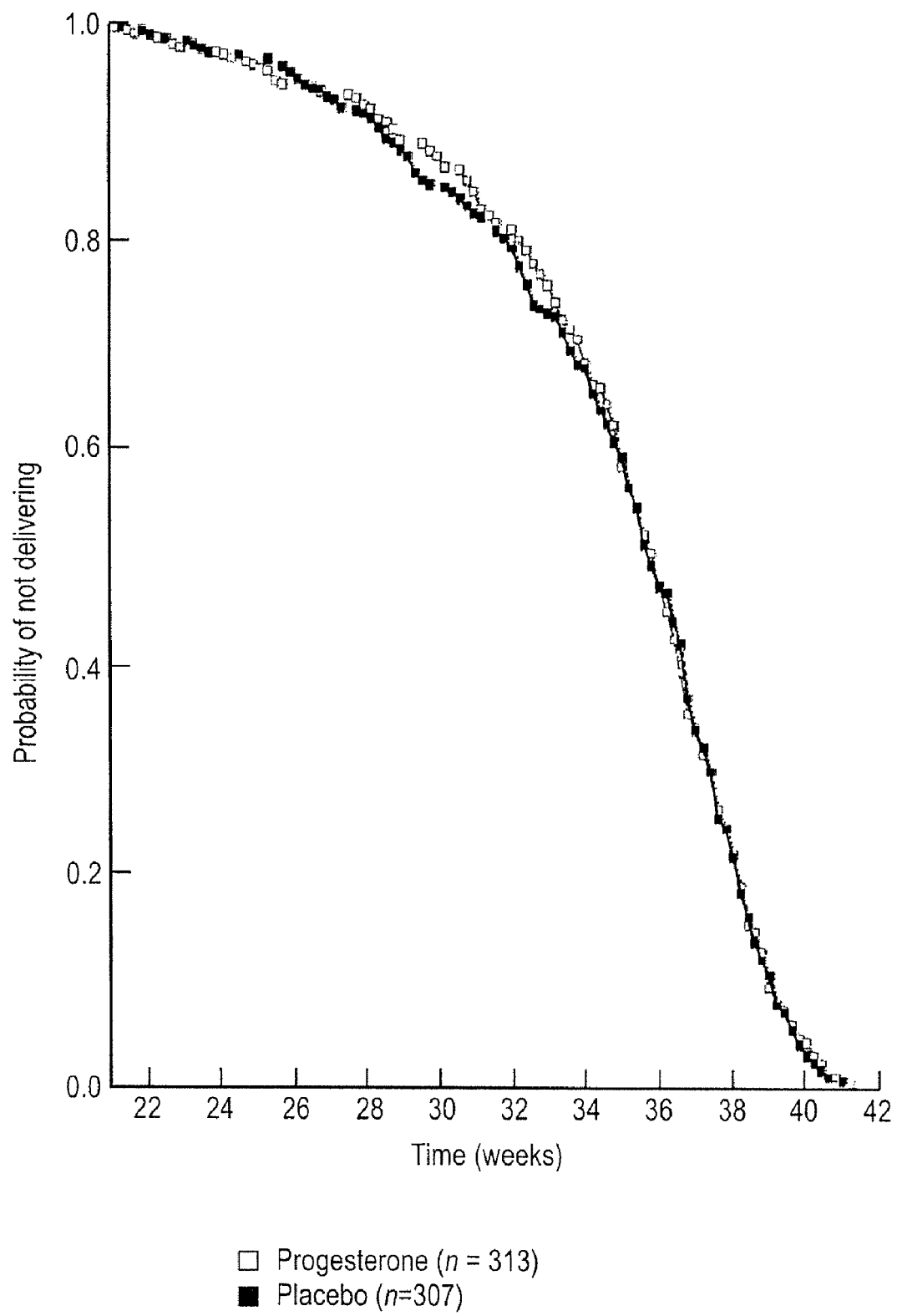
Figure 6:
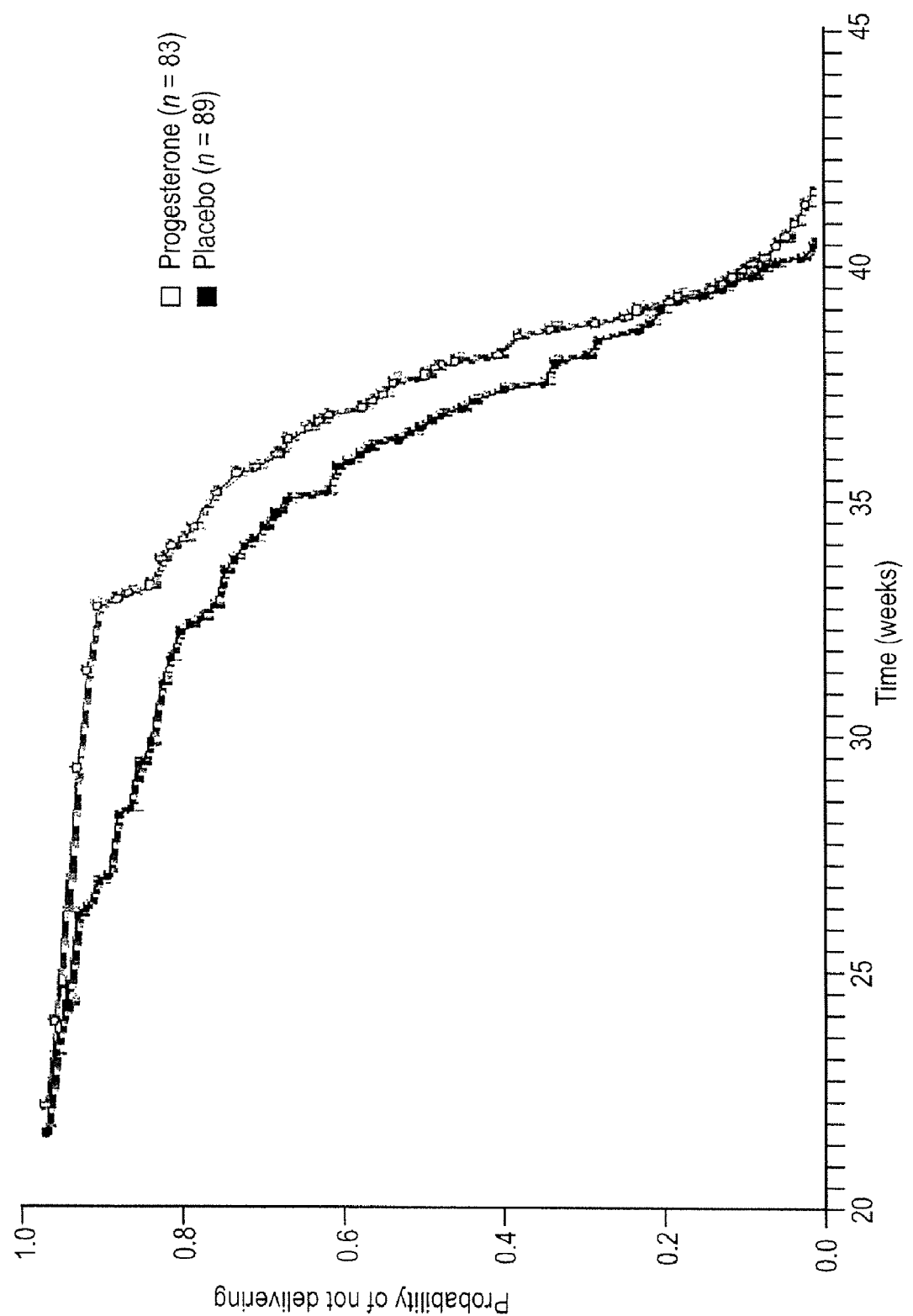
FIG. 6 is a delivery time curve for participants with a baseline cervical length of less than or equal to 3.2 cm, in accordance with one embodiment of the invention.
Figure 7:
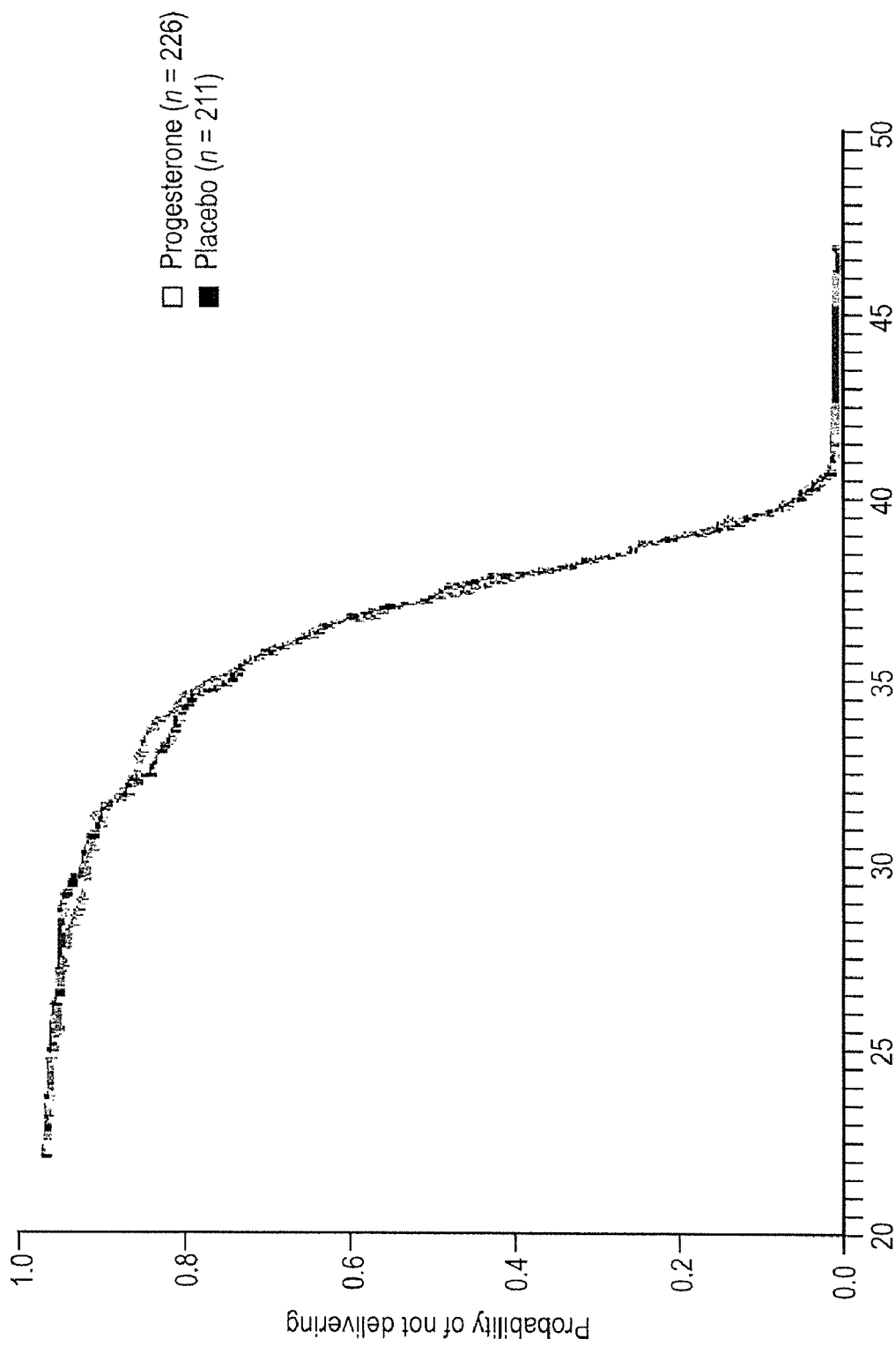
FIG. 7 is a delivery time curve for participants with a baseline cervical length of greater than 3.2 cm, in accordance with one embodiment of the invention.

Without being bound to any theory, it is believed that of all preterm births, women having short cervix account for about 20-30%. The present invention has surprisingly and unexpectedly discovered that the population of women suffering from short cervix among women susceptible, predisposed, or associated with incidence of preterm birth, is responsive to progesterone treatment, prophylaxis, and/or other therapy during pregnancy to prevent, or reduce the incidence, of preterm births. Interestingly, there has been much debate in the art concerning the use of progesterone to reduce the incidence of preterm birth. FIGS. 5a and 5b of this application suggests that there are no differences in gestation period between a treatment population of pregnant women receiving progesterone and a control population receiving placebo, wherein women in both groups have an average baseline cervical length of greater than 3.2 cm. FIGS. 6 & 7 show that the responding population of short cervix patients (see FIG. 6) are hidden in the total population of results (see FIGS. 5a and 5b) and that the longer cervix population patients (see FIG. 7) show no effect of progesterone similar to the overall population (see FIGS. 5a and 5b). That is, the probability of not delivering early in the term is generally similar between the two groups. In fact, statistically, the results are so buried, the prior art teaches away from expecting the results we achieved.

Figure 8:
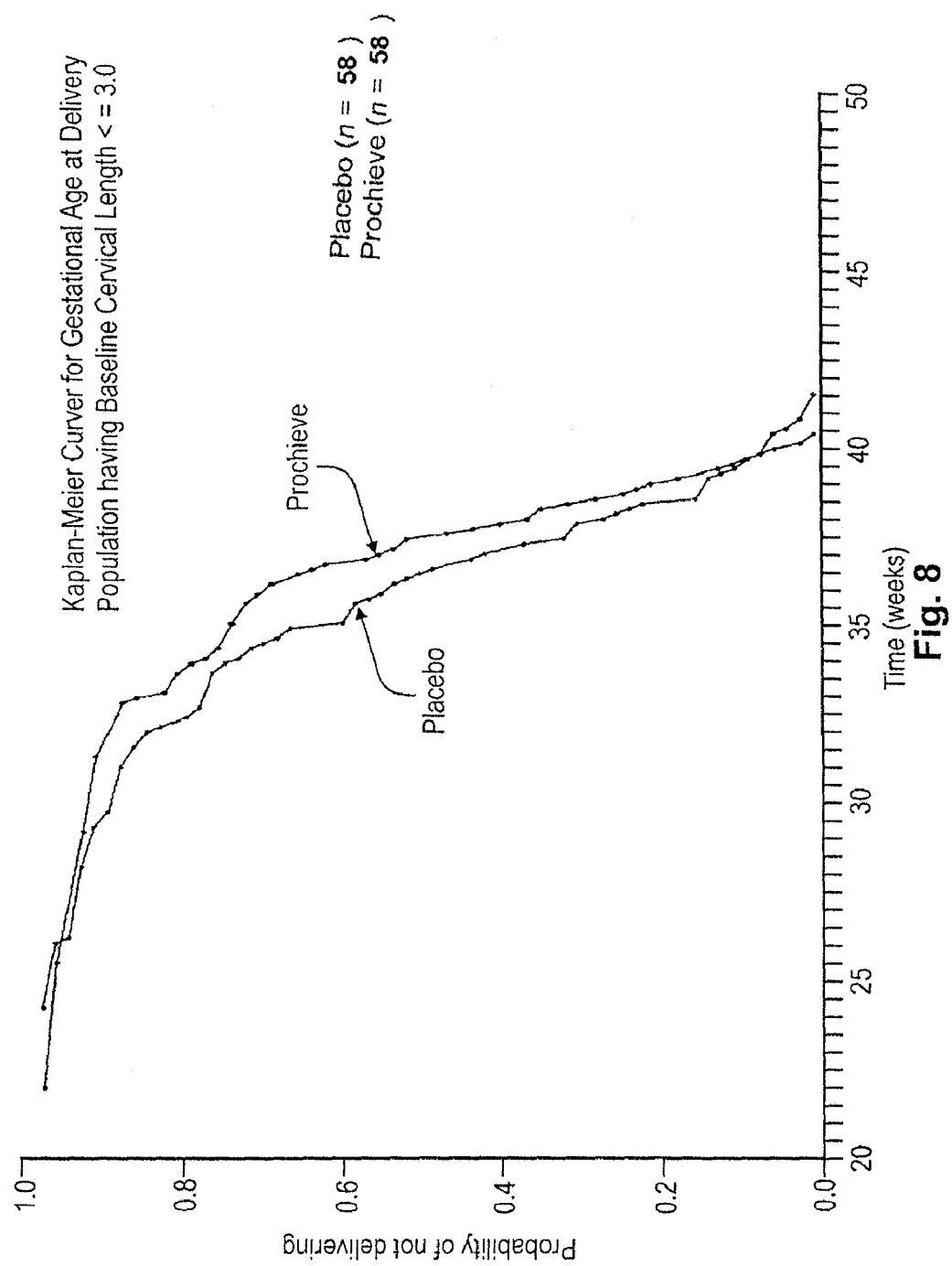
FIG. 8 is a delivery time curve for participants having a baseline cervical length of less than or equal to 3.0 cm, according to one embodiment of the invention.
Figure 9:
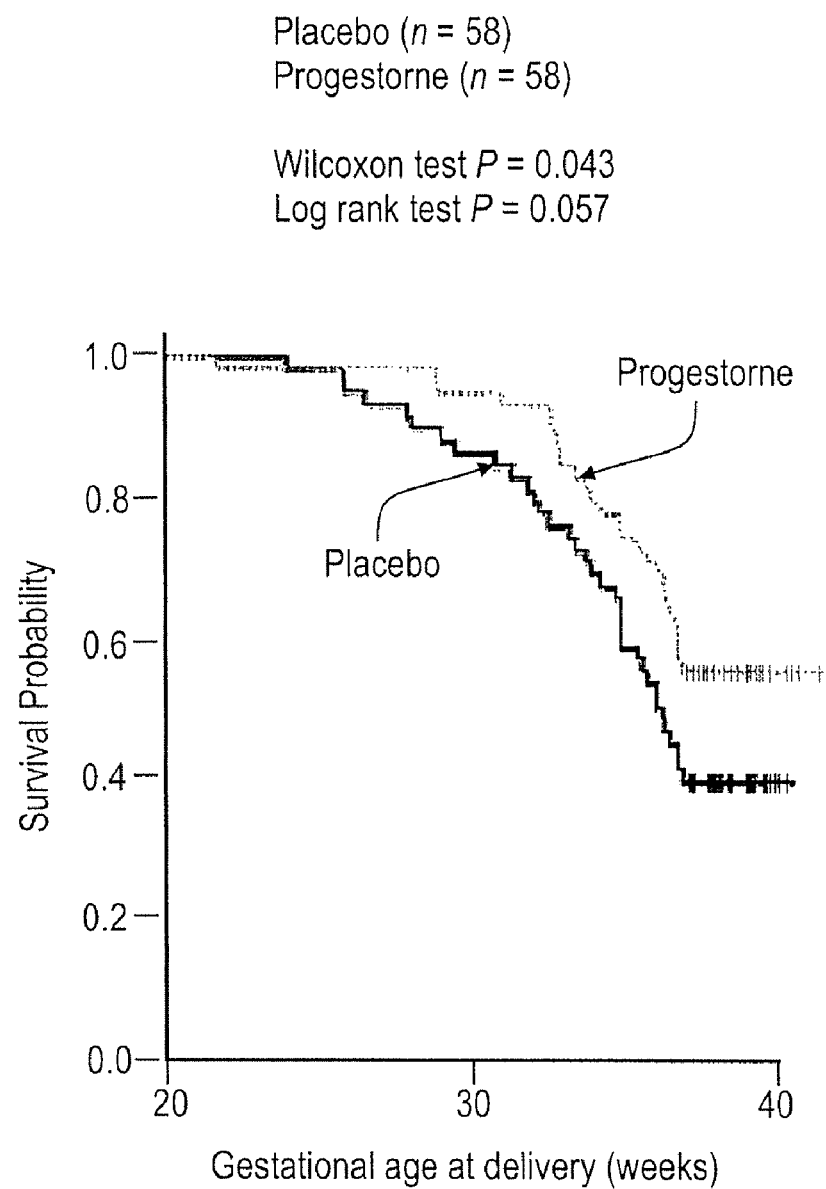
FIG. 9 is a survival curve, evaluating pre-term delivery up to 37 weeks for participants with a cervical length of less than or equal to 3.0 cm, according to one embodiment of the invention.

However, an examination of this short cervix population (e.g., cervical length is less than or equal to 3.0 cm, as shown in FIG. 8, reveals that women receiving progesterone have an increased probability for delivering later during the pregnancy term than women receiving placebo. In FIG. 9, babies born to women who are administered progesterone have a greater chance of survival than babies born to women receiving placebo due to a reduction in preterm birth. See FIGS. 10, 11, and 12. Similar results have been found in women having cervical lengths of less than 2.8 cm.

The progesterone administered in accordance with the present invention can be progesterone molecule (from any source, including natural or synthetic) or progesterone metabolites (from any source, including natural or synthetic), such as 17-alpha-hydroxyprogesterone, for example, or it can be any other progestin. Any combination of these may also be used. In certain embodiments, the term "natural progesterone" includes progesterone and/or a natural progesterone metabolite. Progesterone itself is preferred, although other progestins may be used. Where synthetic progestin is used, preferably, the synthetic progesterone is selected from a group consisting of derivatives of progesterone or of testosterone or derivatives of other molecules and/or compounds with progestogenic activity. The term "derivative" refers to a chemical compound that may be made from or lead to a parent compound resulting from one or more chemical reactions. As used herein, the term "progestin" encompasses natural progesterone, synthetic progesterone, natural or synthetic derivatives of progesterone and/or other progestogenic compounds, or combinations thereof.

Thus progestins include, but are not limited to, 17-alpha-hydroxyprogesterone caproate, medroxyprogesterone acetate, norethindrone, norethindrone acetate, norethindrone enanthate, desogestrel, levonorgestrel, lynestrenol, ethynodiol diacetate, norgestrel, norgestimate, norethynodrel, gestodene, drospirenone, trimegestone, levodesogestrel, gestodyne, nesterone, etonogestrel, and derivatives from 19-nor-testosterone. In a preferred embodiment, the progesterone includes either of the natural progestins, progesterone or 17-alpha-hydroxyprogesterone. Some progestins can be delivered vaginally, some by intramuscular injection, some by oral administration, and some by rectal administration, although other routes of administration can be used as known in the art. In a preferred embodiment, the progesterone is administered via a drug delivery system that comprises progesterone, a water-soluble, water-swellable cross-linked polycarboxylic acid polymer, and at least one adjuvant.

In a preferred embodiment, the progesterone is administered daily, via the vaginal route. However, the administration can be as infrequent as weekly or as often as 4 times daily, depending on the characteristics of the progestin and the progestin formulation, including concentration and routes of administration. Preferably, the progesterone is administered beginning about the $18^{th}$ to $22^{nd}$ week of gestation until about the $37^{th}$ week of gestation, or for approximately 14 to 19 weeks, depending on the gestational age at the beginning of treatment and the date of delivery. In another embodiment, the progesterone is administered beginning about the $16^{th}$ week of gestation until about the $37^{th}$ week of gestation, or for approximately 21 weeks. In still other embodiments, the progesterone is administered beginning about the time of a positive pregnancy test until about the $37^{th}$ week of gestation, or beginning about the $2^{nd}$ to $4^{th}$ week of gestation, for approximately 33 to 35 weeks.

The progesterone is preferably administered to a pregnant woman beginning as early as the onset of gestation and whose cervix has a length greater than about 1.0 cm, or more preferably greater than 1.5 cm. More preferably, the progesterone is administered to a pregnant woman beginning as early as the onset of gestation and whose cervix has a length is at least about 1.0 cm and at most about 8.0 cm, and even more preferably, the progesterone is administered to a pregnant woman whose cervix has a length less than or equal to 3.0 cm or less than or equal to 2.5 cm in more preferable embodiments.

The amount of progesterone administered is preferably between about 45 mg and 800 mg, and more preferably between about 90 mg and 250 mg, based on the progestin effect of natural progesterone administered vaginally, but may be more or less depending on the potency of the progestin, the delivery system, and the route of administration. The concentration of progesterone is from about 0.01% to about 50%, preferably from about 1% to about 40%, more preferably from about 2.5% to about 30%, even more preferably from about 5% to about 20%, and still more preferably from about 6% to about 15%. In the most preferred embodiments, the concentration of progesterone is from about 7% to about 9%.

For some embodiments, the amount and concentration of the progesterone needs to be sufficient to remain in the subject to provide prophylaxis or treatment, such as for about 1 hour or more, preferably greater than about 2 hours, even more preferably greater than 6 hours, still more preferably greater than about 12 hours, yet more preferably greater than about 24 hours, and most preferably greater than about 36 hours.

For some embodiments, the method of administration may include administered, parenterally, by injection, orally, topically, intravenously, intraperitoneally, subcutaneously, transcutaneously, intradermally, subdermally, intra-articularly, intraventricularly, intrathecally, intravaginally, or intramuscularly. Additional formulations that are suitable for other modes of administration include suppositories and, in some cases, through a buccal, sublingual, intraperitoneal, intravaginal, anal or intracranial route. In preferred embodiments, the method of administration is vaginal.

In certain embodiments, the progesterone is provided in solution, such as an oil or otherwise suitable carrier as understood by one skilled in the art. Other methods of delivery, such as oil-based capsules and suppositories, are also available in certain embodiments. For suppositories, any traditional binder and/or carrier may be used, for example, one or more polyalkalene glycols or triglycerides; such suppositories may be formed from mixtures containing the active ingredient in the range of preferably about 0.5% to 10%, more preferably about 1 to 2%. Oral formulations may include such normally employed excipients as, for example, pharmaceutically acceptable mannitol, lactose, starch, magnesium stearate, sodium saccharine, cellulose, magnesium carbonate, and the like, or any combination.

Embodiments of the present invention administer the progesterone as many times per day as needed to be effective to prevent and/or treat preterm birth, i.e., delay birth and increase gestation, preferably more than or equal to 37 weeks. In certain variations of these embodiments, the dosing of progesterone is 1 to 4 times per day. It should understood to one skilled in the art that the frequency of administration per day varies by the concentration and amount of progesterone delivered. For example, 90 mg of 8% progesterone delivery systems are preferably administered once per day. In other embodiments, 200 mg progesterone is administered 2 to 4 times per day.

Some embodiments of the present invention deliver the progesterone together with or in a composition having a pharmaceutically acceptable bioadhesive carrier that comprises a cross-linked carboxylic polymer. Certain variations of these embodiments include a water-swellable polycarboxylic acid polymer, that upon administration provide local directed tissue levels and efficacy without detrimental blood levels of the treating agent.

In preferred embodiments of the present invention, compositions of the present invention are useful for vaginal administration. For example, the vaginal route of administration may be chosen due to its potential for greater patient satisfaction compared with intramuscular dosing, and for improved efficacy through enhanced drug delivery to target tissues. The bioadhesive formulations of the invention have been found to provide local vaginal administration of progesterone useful local drug levels while avoiding levels that give rise to undesirable side effects. Vaginal administration also avoids first-pass metabolism problems, e.g., provides a first uterine pass effect, and direct delivery to the uterus allows for lower systemic drug concentrations.

In preferred embodiments, the progesterone is administered in a bioadhesive formulation of progesterone for vaginal application consisting of a polycarbophil-based gel that contains 8% (wt/wt) progesterone. In the most preferred embodiments, the progesterone is delivered as 8% progesterone gel and placebo, commonly available as Prochieve® or Replens®, which are manufactured by Columbia Laboratories, Inc., NJ. In some embodiments, the progesterone is delivered in a prefilled, single-use, disposable plastic applicator that delivers the dose of 1.125 g of gel containing 90 mg of progesterone. Embodiments of the present invention deliver progesterone in accordance with U.S. Pat. No. 5,543,150 from U.S. patent application Ser. No. 08/122,371, which is incorporated herein in its entirety.

The methods disclosed of the present invention may be used in conjunction with other methods of preventing and/or treating preterm birth and/or short cervix in pregnant women, such as surgical cerclage, administration of complementary/supplementary compositions such as antibiotics, indomethacin, and polymeric compositions, for example. Accordingly, the present invention is suitable for combination therapy.

EXAMPLES

The present invention is further illustrated by the following examples that are merely for the purpose of illustration and are not to be regarded as limiting the scope of the invention or the manner in which it can be practiced. While the results of the study show that progesterone can be effectively administered to pregnant women having baseline cervix lengths between about 1.0 cm and 8.0 cm to treat or prevent the decrease in cervical length during gestation, and thus treat or prevent the onset of preterm labor and premature birth, the following examples show increased efficacy in particular subgroups.

Example 1a

A Randomized, Double Blind, Placebo Controlled Test of the Effects of Progesterone on Preterm Birth In light of the state of the art, a study was conducted to examine the effects of progesterone on preterm labor and premature birth in women with a history of a previous preterm birth. The baseline data for the study is provided in FIG. 1. The participants in the study included 611 evaluable pregnant women, of which 308 were selected into a treatment group and 302 were selected into a placebo group. The selection, categorization, and breakdown of the two groups is outlined in the flow chart of FIG. 2. The study was a prospective, randomized, placebo-controlled, double-blind, multicenter trial in pregnant subjects at high risk of spontaneous preterm delivery. The study participants were screened from 16 0/7 and 22 6/7 weeks gestational age. Subjects were randomized to drug or placebo from 18 0/7 to 22 6/7 weeks.

Subjects meeting the study criteria were enrolled by the investigator between 18 0/7 and 22 6/7 weeks and received identically packaged, sequentially numbered progesterone or placebo vaginal gel in a 1:1 ratio. A SAS (SAS Institute Inc., Cary, N.C., USA) procedure for variable block size was used to generate a randomization schedule stratified by study site and by inclusion criteria (prior preterm birth or short cervix). Quintiles, Inc. (Kansas City, Mo., USA) generated the randomization sequences, which were confidentially provided to the packaging company. Treatment allocation was concealed by an identical packaging and labelling process performed by Aptuit, Inc. (Mount Laurel, N.J., USA). The study patients, obstetric care providers, study investigators, study coordinators, and study monitors were blind to the exposure status (progesterone or placebo) of all study patients.

Once randomized, the subjects began treatment with the allocated study drug and administered it daily until 37 weeks of gestational age, development of preterm rupture of membranes, or delivery. Subjects were randomized in a 1:1 ratio to receive PROCHIEVE® 8% (vaginally administered 90 mg natural progesterone gel) or placebo vaginal gel. All women performed self-dosing on a daily basis of their assigned study medication, either PROCHEIVE® (progesterone) or placebo.

Example 1b

Follow Up Regarding the Randomized, Double Blind, Placebo Controlled Test of the Effects of Progesterone on Preterm Birth The data presented in this Example provides a further examination of the data presented in Example 1a. The objective of this trial was to determine whether prophylactic administration of vaginal progesterone reduces the risk of preterm birth in women with a history of spontaneous preterm birth.

This trial was randomized, double-blind, placebo-controlled, multinational trial enrolled and randomized 659 pregnant women with a history of spontaneous preterm birth alone. Between 18 0/7 and 22 6/7 weeks of gestation, patients were randomly assigned to once-daily treatment with either 8% progesterone vaginal gel or placebo until delivery, 37 weeks gestational age, or development of preterm rupture of membranes (PROM). The primary outcome was preterm birth at ≦32 weeks of gestation. Statistical analysis was based on the intent-to-treat principle.

Pregnant women were eligible to enter the trial if they were between 18 and 45 years of age with an estimated gestational age between 16 0/7 and 22 6/7 weeks, and had a history of spontaneous singleton preterm birth between 20 0/7 and 35 0/7 weeks of gestation in the immediately preceding parity confirmed by review of medical records from the qualifying preterm birth. Patients were also required to understand English or a common local language, provide a voluntarily signed informed consent form, demonstrate an understanding of the purpose of the study, and agree to adhere to the study protocol.

Patients were excluded from the trial if they had a history of an adverse reaction to progesterone or any component present in the treatment drug; had received treatment with progesterone within 4 weeks preceding enrollment; or were currently being treated for a seizure disorder, psychiatric disorder, or chronic hypertension at enrollment. Patients were also excluded from the trial if they had a history of acute or chronic congestive heart failure, renal failure, or uncontrolled diabetes mellitus; an active liver disorder; an HIV infection with a CD4 count <350 cells/mm$^3$ and requiring multiple antiviral agents; a placenta previa or low-lying placenta requiring vaginal precautions; a history or suspicion of breast or genital tract malignancy; a history or suspicion of thromboembolic disease; or a müllerian anomaly. Patients who were currently or previously enrolled in another investigational study within 1 month prior to screening for the present study were not included in the trial. Patients were also restricted from participation in the trial if the present pregnancy was complicated by a major fetal anomaly or a known chromosome disorder, or was a multifetal gestation. Patients with a cervical cerclage in place, or those intending to have one placed during the current pregnancy, were excluded from study participation, as were those with signs of preterm rupture of membranes, vaginal bleeding, amnionitis, or preterm labor at enrollment. Finally, patients who were unable or unwilling to comply with the study procedures or had a qualifying preterm delivery that occurred without preterm labor were not included in the trial.

The study drug was packaged and labelled according to the 1:1 randomization scheme provided by Quintiles, Inc (Kansas City, Mo., USA). A SAS (SAS Institute Inc., Cary, N.C., USA) procedure for variable block size was used to generate the randomization schedule stratified by study site. Thirty-three of the 53 centers completed at least 1 randomized block accounting for 92% of the enrolled patients. The study drug (Prochieve® 8% progesterone gel) and placebo (Replens®) were provided by Columbia Laboratories, Inc. (Livingston, N.J., USA). Patients were instructed to self-administer the full applicator of vaginal gel at approximately the same time daily, preferably in the morning. Patients received a 2-week supply of the allocated treatment at the time of randomization, and at every 2-week study visit thereafter. All drug supplies were to be brought in at each visit at all study centers, and compliance with the study medication was determined from returned empty wrappers and unused wrappers. Percent compliance was assessed as total treatment duration compliance: (total applicators used/total dosing days)×100. Total dosing days was defined as the interval from enrollment to either the date of preterm premature rupture of membranes, the date of preterm birth without accompanying ruptured membranes, or 37 0/7 weeks' gestation.

The occurrence of adverse events was queried at each 2-week study visit at all centers by asking if the patient had any complaints or problems. Subjects received an extra 1-week drug supply when treatment was initiated in case they could not make the next regularly scheduled appointment. The study drug preparation is a bioadhesive formulation of progesterone for vaginal application consisting of a polycarbophil-based gel that contains 8% (wt/wt) progesterone. A prefilled, single-use, disposable plastic applicator delivers the dose of 1.125 g of gel containing 90 mg of progesterone. The placebo was Replens®, the bioadhesive delivery system without the progesterone.

Subjects with a documented history of spontaneous preterm birth were screened between 16 0/7 and 22 6/7 weeks of gestation by the investigator or study coordinator. The gestational age was based on the patient's last menstrual period and correlated with an ultrasound biometry algorithm. Each patient had at least one ultrasound examination before randomization to confirm gestational age and rule out major fetal anomalies, and a transvaginal scan to determine the length of the cervix. Subjects meeting the study criteria were enrolled by the investigator between 18 0/7 and 22 6/7 weeks to receive blinded study medication. Following randomization, daily treatment was initiated by the patient and continued until 37 0/7 weeks' gestational age, occurrence of preterm rupture of the membranes, or preterm delivery. Each patient was evaluated at 2-week intervals. At 28 weeks of gestation all subjects had another transvaginal ultrasound to determine cervical length.

Baseline characteristics were similar in the two treatment groups. Progesterone did not decrease the frequency of preterm birth at ≦32 weeks. There was no difference in the mean gestational age at delivery, infant morbidity or mortality, or other maternal or neonatal outcome measure. Treatment emergent adverse events were similar for the two groups.

Based on these results, prophylactic treatment with vaginal progesterone gel does not effectively reduce the frequency of recurrent preterm birth in high-risk women selected by a history of spontaneous preterm birth. Other methods of risk assessment need to be studied.

A determination of the exact number of patients pre-screened at all 53 study sites, including referral offices to these sites, was not considered feasible. An estimate of 1500 pre-screened subjects was obtained by querying the study sites. A total of 711 women were defined as formally screened (informed consent obtained but not randomized), and 42 were subsequently excluded. The most common reasons for exclusion after consent were planned cerclage, comorbid conditions, and failure to document previous spontaneous preterm birth at a qualifying gestational age. A total of 669 patients were considered eligible for enrollment into the study, with 659 randomized to the two treatment groups indicated for maternal history alone (FIG. 2). Nine patients enrolled into the planned subinvestigation for short cervix alone and one qualifying patient lost to follow-up prior to randomization were excluded from the analysis. Patients who took at least one dose of study medication and provided a delivery date were included in the intent-to-treat (ITT) population. Patients without a delivery date were considered lost to follow-up.

The ITT population for previous preterm birth patients included 309 patients in the progesterone group and 302 patients in the placebo group. The randomization provided treatment groups that were well matched for age, ethnicity, and body mass index (BMI). Parity, number of prior preterm births, and spontaneous abortions were also similar. The mean (±SD) gestational age at randomization was 19.9 (±2.1) and 20.1 (±3.3) weeks for the progesterone and placebo groups, respectively. With regard to prior pregnancy history, 76.4% of progesterone patients and 74.5% of placebo patients had one previous spontaneous preterm birth, and 23.6% and 25.5% of subjects in each group had two or more previous preterm births, respectively.

The rate of preterm birth at ≦32 0/7 weeks of gestation, the primary outcome, was not significantly different; 10.0% (n=31) in the progesterone group and 11.3% (n=34) in the placebo group. In the analysis of the primary outcome by country/region, no significant difference existed between a country or region was observed. The mean gestational age at delivery was 36.6 weeks for both the progesterone and placebo groups. Compliance rates with the study medication were also similar: 96.2% for women in the progesterone group and 96.4% for women in the placebo group.

Other study outcomes also did not differ between the progesterone and the placebo groups. The rate of preterm birth was 41.7% (n=129) versus 40.7% (n=123), respectively, at <37 0/7 weeks; 22.7% (n=70) versus 26.5% (n=80), respectively, at ≦35 0/7 weeks; and 3.2% (n=10) versus 3.0% (n=9), respectively, at ≦28 0/7 weeks. The survival curves for time to delivery are shown in FIG. 5a. Admissions for preterm labor (25.6% for progesterone vs. 24.8% for placebo), administration of tocolytic medications, and administration of antepartum corticosteroid therapy were similar between the two groups. In patients admitted for treatment of preterm labor, the number of days from admission to delivery was 30 for progesterone and 19.6 for placebo (95% CI, -23-2.3). In addition, there were no differences in the rate of preterm rupture of membranes (12.0% vs. 12.6%) or stillbirth/intrauterine fetal demise (1.6% vs. 1.3%) in the progesterone and placebo groups, respectively.

The mean birth weight of the neonates in the progesterone and placebo groups was similar (2680±710 vs. 2661±738 gm, respectively), as was head circumference (32.3±3.34 vs. 32.5±3.75 cm, respectively). There were no differences between treatment and placebo groups for the 1-minute (median score=8 for each) and 5-minute (median score=9 for each) APGAR scores, or the rate of admission to a neonatal intensive care unit (17.5% vs. 21.5%). Occurrences of newborn respiratory distress syndrome (11.0% vs. 11.9%), grade 3 or 4 intraventricular haemorrhage (0.3% vs. 0.3%), and necrotizing enterocolitis (1.0% vs. 1.7%) were also similar for the progesterone and placebo groups. Congenital abnormalities potentially acquired in the second or third trimesters were observed in 2 newborns: 1 case each of hip subluxation and pulmonic stenosis in each group. Developmental abnormalities related to first-trimester organogenesis, such as hypospadias, extra digits, and tetralogy of Fallot, were not included. Infant follow-up data for 6, 12, and 24 months of age are still being collected and not available at the time of reporting of these results.

Example 2

Randomized Trial Investigating the Efficacy of Vaginal Progesterone to Prevent Early Preterm Birth in Women with a Shortened Cervix in the Midtrimester The study further included women without a history of preterm birth and having a short cervix at the time of enrollment. Although the short cervix only population included 9 patients, the results suggested a possible effect of progesterone with 40% (2/5) delivering ≦32 weeks gestation on placebo and 0 (0/4) delivering ≦32 weeks gestation on progesterone. As some participants with a history of prior preterm birth also had a short cervix, the preterm birth study population was divided into quartiles based on cervical length. The lowest quartile (≦3.2 cm) was combined with the short cervix only patients and subdivided sequentially and the primary and secondary outcomes for women with cervical lengths of ≦3.0 cm and <2.8 cm at the time of enrollment were analyzed. There were an insufficient number of patients with even shorter cervical lengths available for further analysis. For the purposes of the study, the criteria for short cervix was set at less than 2.8 cm. A total of 46 participants fell into this category, and their demographics and characteristics are set forth in FIG. 3.

Generally, a cervical length <2.8 cm was identified in 46 randomized women: 19 of 313 who received progesterone and 27 of 307 who received placebo. Baseline characteristics of the two groups were similar. The rate of preterm birth at ≦32 weeks was significantly lower for progesterone than placebo (0% vs. 29.6%, P=0.014). With progesterone, there were fewer NICU admissions (15.8% vs. 51.9%, P=0.016) and shorter NICU stays (1.1 vs. 16.5 days, P=0.013). There was also a trend toward a decreased rate of neonatal respiratory distress syndrome (5.3% vs. 29.6%, P=0.060). It was determined that vaginal progesterone gel reduces the rate of early preterm birth and improves neonatal outcome in women with mid-trimester cervical shortening.

The study included women with a documented history of spontaneous preterm birth (<35 weeks) in a singleton pregnancy in the immediate preceding parity regardless of cervical length, and women without a history of preterm birth but with midtrimester cervical shortening (≦2.5 cm) in the current pregnancy were offered enrollment in the study at 18 0/7-22 6/7 weeks of gestation. Recruitment began in April 2004 and the last patient delivered Jan. 8, 2007.

Women were excluded from the study if they had a condition or complication of pregnancy prior to screening that increased the maternal or fetal risk of an adverse outcome, significantly increased the risk of a medically indicated (non-spontaneous) preterm birth, or would likely result in lack of compliance or early discontinuation of the study. Therefore, women were excluded if any of the following conditions were present: age <18 or >45 years; multifetal gestation; history of an adverse reaction to progesterone or any component present in the treatment medication; treatment with progesterone within 4 weeks preceding enrollment; or current treatment for a seizure disorder, psychiatric disorder, or chronic hypertension. Patients were also excluded from the trial if they had a history of acute or chronic congestive heart failure, renal failure, or uncontrolled diabetes mellitus; an active liver disorder; an HIV infection with a CD4 count <350 cells/mm$^3$ and requiring multiple antiviral agents; a placenta previa or low-lying placenta and placed on vaginal precautions; a history of breast or genital tract malignancy; a thromboembolism; or a müllerian anomaly. Patients who were currently or previously enrolled in another investigational study within one month prior to randomization were not included.

Patients were also restricted from participation in the trial if the present pregnancy was complicated by a major fetal anomaly or a known chromosome disorder. Patients with a cervical cerclage in place, or those intending to have one placed during the current pregnancy, were excluded from the study, as were those with signs of preterm rupture of membranes, vaginal bleeding, amnionitis, or preterm labor at enrollment.

Women with a history of spontaneous preterm birth in the preceding pregnancy regardless of cervical length or women without a history of preterm birth but with midtrimester cervical shortening in the current pregnancy were screened by the investigator or study coordinator between 16 0/7 and 22 6/7 weeks of gestation. Prior history of spontaneous preterm birth was confirmed by evaluation of the patient's medical records before enrollment. Gestational age was based on the patient's last menstrual period and correlated with an ultrasound biometry algorithm. Each patient had at least one ultrasound examination before randomization to confirm gestational age and rule out major fetal anomalies, and a transvaginal scan to determine the length of the cervix. Subjects meeting the study criteria were enrolled by the investigator between 18 0/7 and 22 6/7 weeks and received identically packaged, sequentially numbered progesterone or placebo vaginal gel in a 1:1 ratio. A SAS (SAS Institute Inc., Cary, N.C., USA) procedure for variable block size was used to generate a randomization schedule stratified by study site and by inclusion criteria (prior preterm birth or short cervix). Quintiles, Inc. (Kansas City, Mo., USA) generated the randomization sequences, which were confidentially provided to the packaging company. Treatment allocation was concealed by an identical packaging and labelling process performed by Aptuit, Inc. (Mount Laurel, N.J., USA). The study patients, obstetric care providers, study investigators, study coordinators, and study monitors were blind to the exposure status (progesterone or placebo) of all study patients.

Following randomization, daily treatment was initiated by the patient and continued until 37 0/7 weeks' gestational age, occurrence of preterm rupture of membranes, or delivery. Each patient was evaluated at 2-week intervals. All subjects had another transvaginal ultrasound to determine cervical length at 28 weeks of gestation.

Prior to beginning the study, baseline measurements of each of the participant's cervical length were taken and are summarized in FIG. 1. During the study, cervical length measurements were made by ultrasound at both baseline and later at 28 weeks after a period of 6-10 weeks of dosing. The mean cervix length of 3.7 cm was the same for both the treatment and placebo groups, and the range of cervical length for all participants was between 1.1 cm and 7.9 cm. At 28 weeks gestation, each participant's cervix was re-measured and the data was compared to the baseline data, and an unexpected and surprising finding was discovered. As shown in FIG. 4, the mean decrease in cervix length after 28 weeks for participants in the placebo group was 0.61 cm, while the mean decrease in cervix length over the same period of time for those participants in the treatment group (i.e., on the progesterone regimen) was only 0.44 cm. Because the p-value for the overall test was 0.038, the results indicate that there was a statistically significant decrease in the amount of shortening or effacing of the cervix length for women on the progesterone regimen compared to women taking placebo.

The results of the study are depicted using Kaplan-Meier curves as shown in FIGS. 5b-10, examining the preterm birth endpoint in the study. FIG. 5b is a curve for time to delivery for all randomized patients. Though the curves for each group in FIG. 5b appear to have substantial overlap, when the results are broken down further for analysis by patient cervical length at baseline, the difference in outcome between the treatment and placebo groups is clearly visible. For patients having a baseline cervical length of less than or equal to 3.2 cm, (FIG. 6), less than or equal to 3.0 cm (FIGS. 8 and 9), and less than 2.8 cm (FIG. 10), participants in the treatment group clearly exhibited a probability of not delivering over a longer gestation period compared to participants in the placebo group. As shown in FIG. 7, no statistically significant difference in outcome was reflected between the treatment and placebo groups in patients having a baseline cervical length greater than 3.2 cm at baseline.

Figure 10:
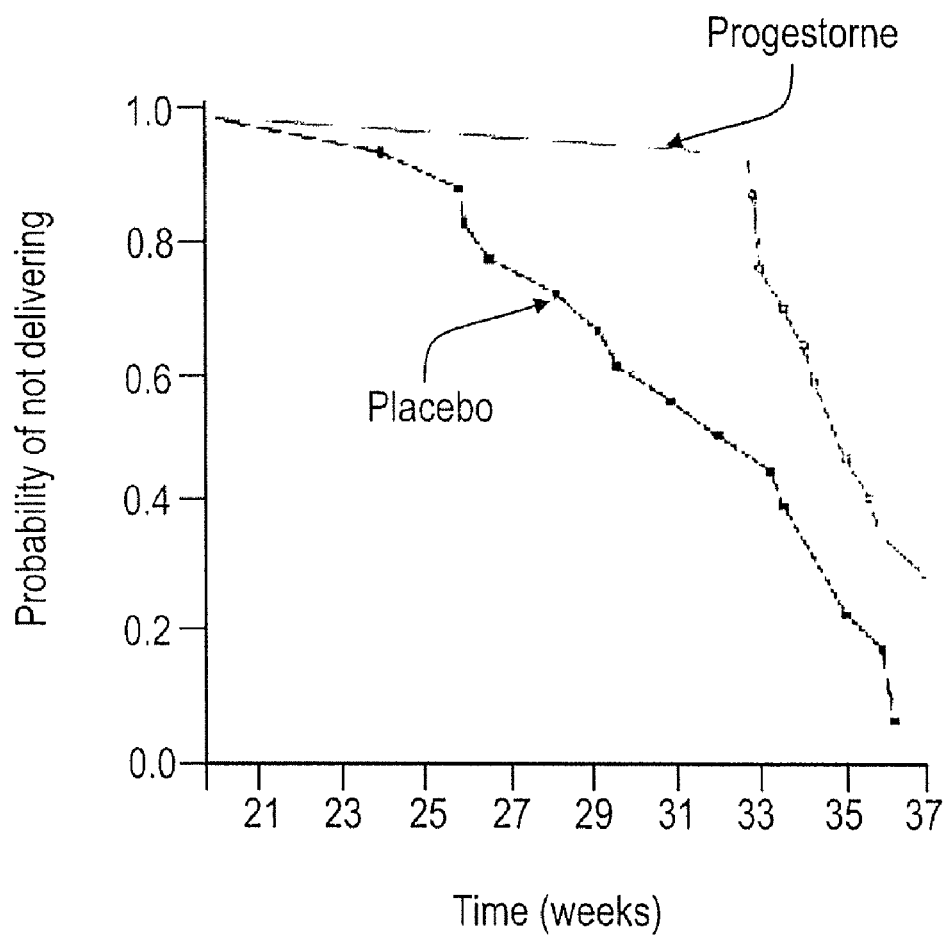
FIG. 10 is a delivery time curve for participants having a cervical length of less than 2.8 cm, according to one embodiment of the invention.
Figure 13B:
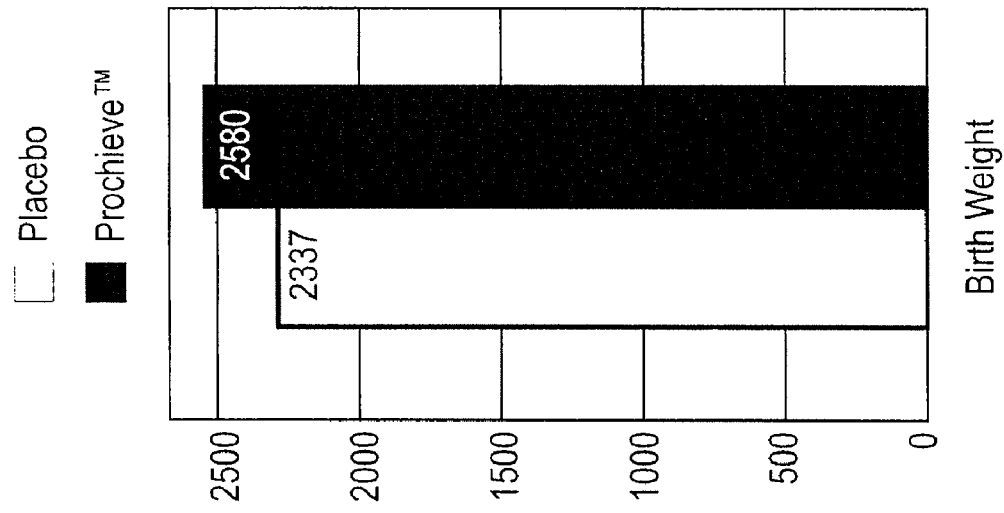
FIGS. 13a-e present graphs depicting infant outcomes in placebo and treatment patients with a baseline cervical length $\leq$3.0 cm, in accordance with one embodiment of the present invention.
Figure 13A:
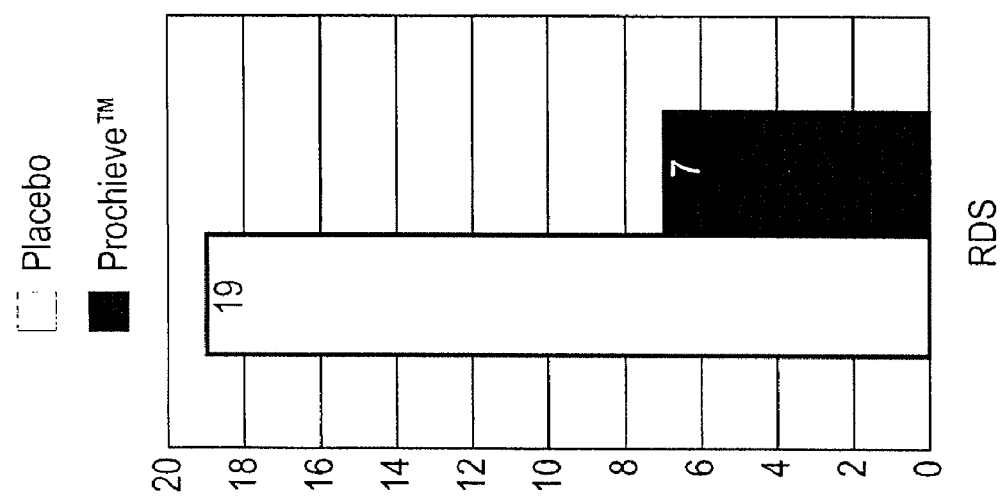
Figures 13C, 13D, 13E:
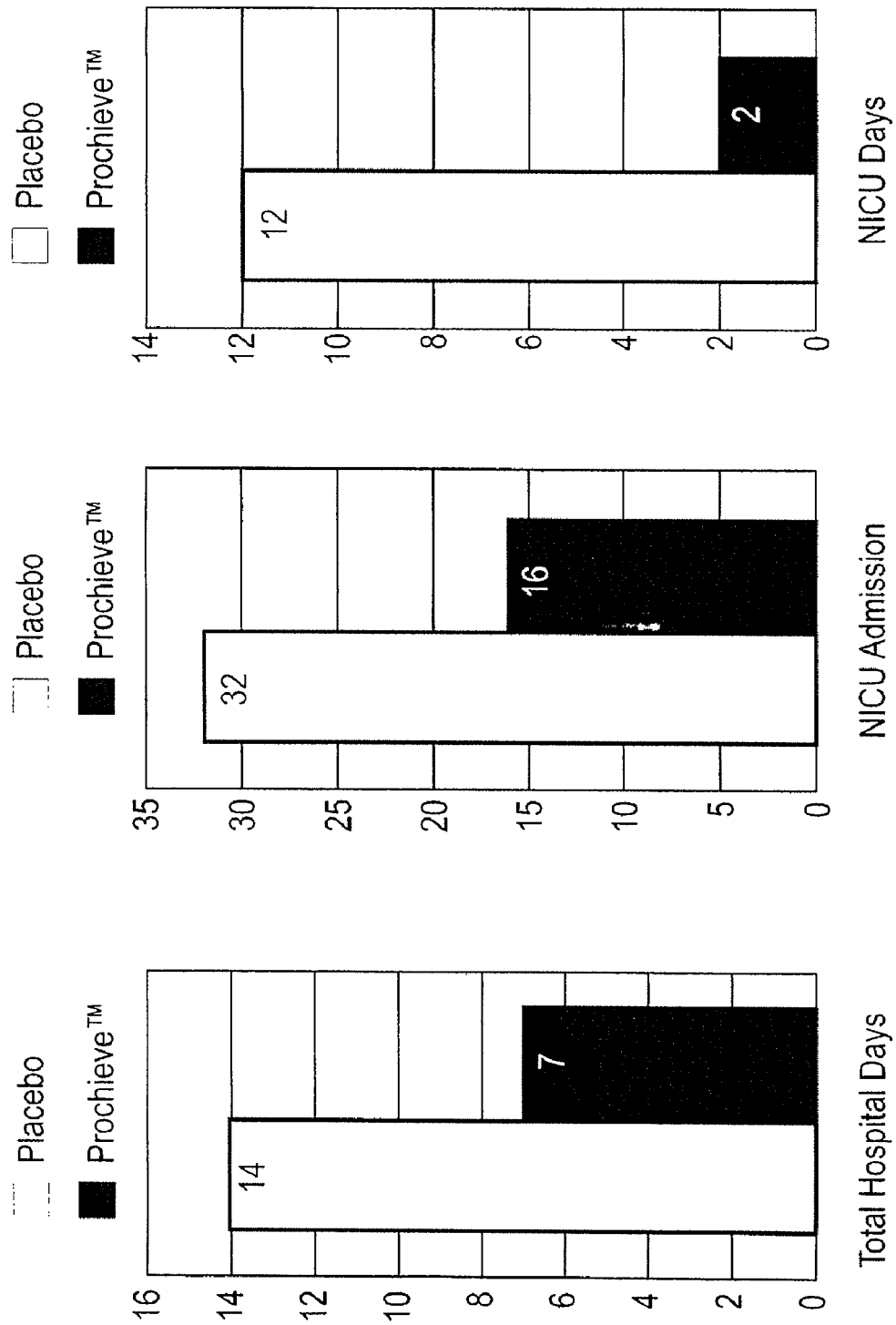
Figure 14E:
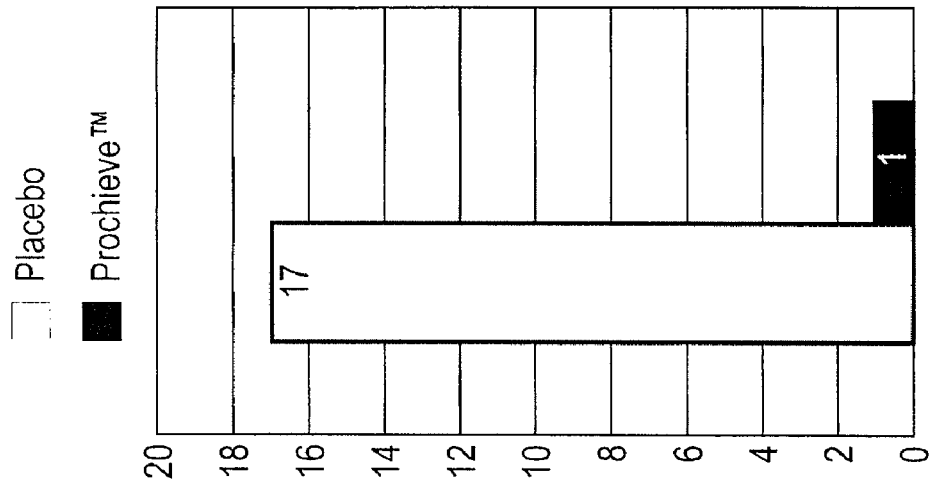
Figure 14D:
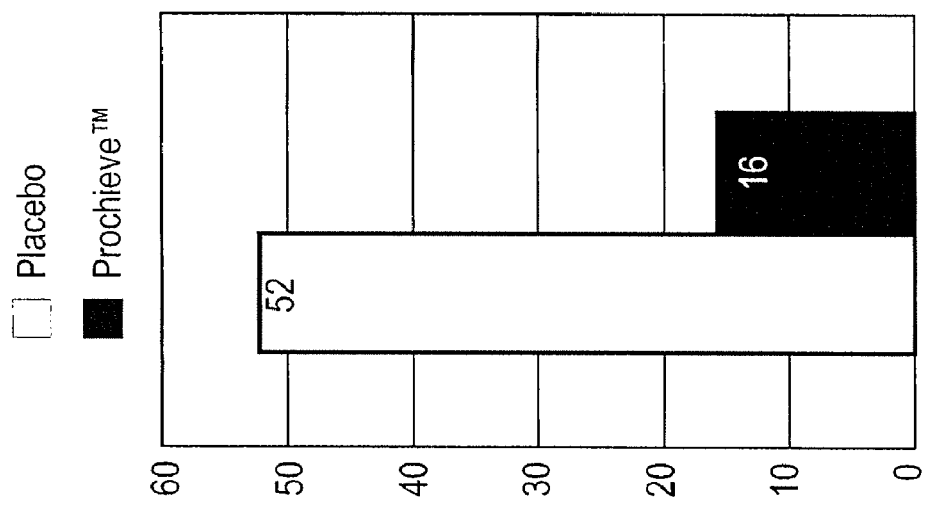
Figure 14C:
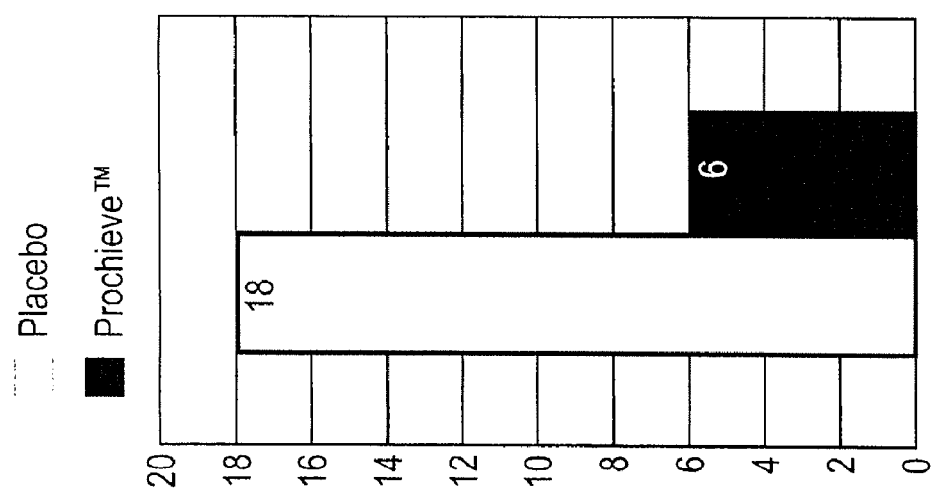

Referring to FIG. 10, which shows the probability of patients with baseline cervical length less than 2.8 cm remaining undelivered, the participant group having a cervical length of less than 2.8 cm experienced a significant reduction in the frequency of preterm birth. As shown in FIG. 10, among 46 subjects (19 treated with progesterone, e.g., Prochieve® brand progesterone, and 27 placebo) the frequency of preterm birth in the treatment group was 0%, vs. 29.6% in the placebo group (P=0.014). For the purposes of this study, parameter for preterm birth was set at less than or equal to 32 weeks. FIG. 11 includes a more detailed breakdown of delivery at various points of gestation for the progesterone and the placebo groups, namely for less than or equal to 37, 35, 32, and 28 weeks. The outcome was markedly improved for the treatment group over the placebo group at each time point. Specifically, for less than or equal to 37 and less than 35 weeks, treatment reduced the number of preterm delivery by about half, and for less than or equal to 32 and less than or equal to 28 weeks, there were no preterm deliveries in the treatment group, though there were 8 and 3 preterm deliveries, respectively, in the placebo group.

Study results also revealed an improved outcome for neonates born to participants in the progesterone group, which is shown in FIG. 12. When administered to women with a cervical length <2.8 cm, progesterone therapy reduced the number of admissions to the NICU (15.8% vs. 51.9%, P=0.016) and decreased the length of NICU stay (1.1 vs. 16.5 days, P=0.013). There was a trend toward a reduction in total neonatal hospital days (5.8 vs. 18.2 days, P=0.055) and decreased occurrence of neonatal respiratory distress syndrome (5.3% vs. 29.6%, P=0.060) with progesterone therapy.

In the subgroup of women enrolled with a cervical length of <2.8 cm, 2 fetal/infant deaths occurred in the placebo group ([1] term, expired at 11 months of age, SIDS; [2] 35 weeks of gestation, aspiration pneumonia) and none in the vaginal progesterone group.

Based on the results of this study, it is evident that administering progesterone to pregnant women effectively decreases the amount of shortening or effacing of their cervixes, most notably in women with short cervixes.

Example 3

Population Having a Baseline Cervical Length of <2.8 cm

The data for a subgroup of participants having a baseline cervical length of less than or equal to 2.8 cm is provided in Table 1 below. The results show that 8 of the 27 participants who received the placebo regimen gave birth earlier than 32 weeks, while none of the 19 participants who received the progesterone regimen gave birth earlier than 32 weeks. As indicated by the two-sided p-value of 0.014 and the 95% CI −0.469, −0.124, the results indicate the statistically significant effect in the reduction of births before 32 weeks by administration of progesterone compared to placebo among a population of pregnant women having a baseline cervical length of ≦2.8 cm. See also FIGS. 12 and 14a-e, which provide a comparison between treatments for infant outcomes of patients using placebo versus patients using Prochieve® progesterone.

TABLE 1

|  |  | Births >32 Weeks | Births ≦32 Weeks | Total |
|---|---|---|---|---|
| Placebo Group | Number | 19 | 8 | 27 |
| Treatment Group | Number | 19 | 0 | 19 |
|  | Total | 38 | 8 | 46 |
|  |  |  | Fisher's Exact Test p-Value | 0.014 |
|  |  |  | 95% CI | −0.469, −0.124 |

Example 4

Population Having a Baseline Cervical Length of ≦3.0 cm

The data for a subgroup of participants having a baseline cervical length of less than or equal to 3.0 cm is provided in Table 2 below. The results show that 11 of the 58 participants who received the placebo regimen gave birth at 32 weeks or earlier, while only 4 of the 58 participants who received the progesterone regimen gave birth at 32 weeks or earlier. These results are significant according to the 95% CI and the 2-sided p-value indicates a trend for the effect in the reduction of births before 32 weeks by administration of progesterone compared to placebo among the population of pregnant women having a baseline cervical length of ≦3.0 cm. See also FIGS. 13a-e, which provide a comparison between treatments for infant outcomes of patients using placebo versus patients using Prochieve® progesterone.

TABLE 2

|  |  | Births >32 Weeks | Births ≦32 Weeks | Total |
|---|---|---|---|---|
| Placebo Group | Number | 47 | 11 | 58 |
| Treatment Group | Number | 54 | 4 | 58 |
|  | Total | 101 | 15 | 116 |
|  |  |  | Two-sided Pr ≦ P | 0.094 |
|  |  |  | 95% CI | −0.214, −0.001 |

The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the spirit and scope of the present invention.

The invention claimed is:

1. A method for treating short cervix in a pregnant woman in order to treat the onset of preterm labor and subsequent preterm birth comprising:
    administering an effective amount of a formulation containing progesterone sufficient to prolong gestation by minimizing the shortening or effacing of the cervix.

2. The method of claim 1, wherein the method further comprises monitoring or confirming the reduction in cervical shortening or effacement after the administration of said progesterone.

3. The method of claim 1, wherein the formulation is administered vaginally and is:
    a) in the form of a gel, cream, suppository, or solid dosage form; or
    b) is released by a suitable delivery device.

4. The method of claim 1, wherein the progesterone comprises one or more of the following: a natural progesterone, or a synthetic progesterone.

5. The method of claim 4, wherein the progesterone is natural progesterone.

6. The method of claim 5, wherein said natural progesterone is administered vaginally.

7. The method of claim 4, wherein the progesterone comprises one or more synthetic progesterones.

8. The method of claim 7, wherein said synthetic progesterone is administered vaginally.

9. The method of claim 7, wherein said synthetic progesterone is selected from a group consisting of one or more of the following: medroxyprogesterone acetate, norethindrone, norethindrone acetate, norethindrone enanthate, desogestrel, levonorgestrel, lynestrenol, ethynodiol diacetate, norgestrel, norgestimate, norethynodrel, gestodene, drospirenone, trimegestone, levodesogestrel, gestodyne, nesterone, etonogestrel, and derivatives from 19-nor-testosterone.

10. The method of claim 1, wherein said progesterone is administered daily beginning about the $18^{th}$ to $22^{nd}$ week of gestation until about the $37^{th}$ week of gestation.

11. The method of claim 1, wherein the amount of progesterone that is administered is between about 45 mg and 800 mg.

12. The method of claim 1, wherein the progesterone is administered via a drug delivery system that comprises progesterone, a water-soluble, water-swellable cross-linked polycarboxylic acid polymer, and at least one adjuvant.

13. The method of claim 1, wherein the progesterone is administered to a pregnant woman whose cervix has a length between 1.0 cm and 2.8 cm.

14. The method of claim 1, wherein the progesterone is administered to a pregnant woman whose cervix has a length between 1.0 cm and 3.0 cm.

15. The method of claim 1, wherein the progesterone comprises both natural progesterone and 17-alpha-hydroxyprogesterone caproate.

16. The method of claim 15, wherein the progesterone is administered beginning about the $2^{nd}$ to $4^{th}$ week of gestation.

17. The method of claim 11, wherein the progesterone is administered as early as gestation.

18. The method of claim 11, wherein the amount of progesterone that is administered is about 90 mg and the progesterone is natural progesterone administered vaginally.

19. A method for treating short cervix in a pregnant woman in order to treat the onset of preterm labor and subsequent preterm birth comprising:
    administering an effective amount of a formulation containing progesterone sufficient to prolong gestation by minimizing the shortening or effacing of the cervix.

20. A method for treating short cervix in a pregnant woman in order to treat the onset of preterm labor and subsequent preterm birth comprising:
    determining to treat short cervix in a pregnant woman in order to maintain or prolong gestation; and
    administering an effective amount of a formulation containing progesterone sufficient to prolong gestation by minimizing the shortening or effacing of the cervix.

* * * * *